US009339244B2

United States Patent
Takata et al.

(10) Patent No.: US 9,339,244 B2
(45) Date of Patent: May 17, 2016

(54) PRESS PLATE AND RADIOGRAPHIC IMAGING APPARATUS

(71) Applicant: FUJIFILM Corporation, Tokyo (JP)

(72) Inventors: Kenji Takata, Kanagawa (JP); Shinji Otokuni, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 136 days.

(21) Appl. No.: 14/033,899

(22) Filed: Sep. 23, 2013

(65) Prior Publication Data
US 2014/0093034 A1 Apr. 3, 2014

(30) Foreign Application Priority Data
Sep. 28, 2012 (JP) .................................. 2012-218265

(51) Int. Cl.
*A61B 6/04* (2006.01)
*A61B 6/00* (2006.01)
(52) U.S. Cl.
CPC .................. *A61B 6/04* (2013.01); *A61B 6/0414* (2013.01); *A61B 6/502* (2013.01); *A61B 6/544* (2013.01); *A61B 6/545* (2013.01); *A61B 6/542* (2013.01)
(58) Field of Classification Search
USPC ....................................... 378/1, 37, 177, 208
See application file for complete search history.

(56) References Cited

U.S. PATENT DOCUMENTS

| 2005/0008117 A1 | 1/2005 | Livingston |
| 2008/0043904 A1 | 2/2008 | Hoernig |
| 2008/0080668 A1 | 4/2008 | Kashiwagi |
| 2014/0093033 A1* | 4/2014 | Takata et al. .................... 378/37 |

FOREIGN PATENT DOCUMENTS

| JP | 2007-135704 A | 6/2007 |
| JP | 2008-086451 A | 4/2008 |
| JP | 2011-206438 A | 10/2011 |

OTHER PUBLICATIONS

Japanese Office Action dated Aug. 26, 2014 with a partial English translation thereof.
Extended European Search Report dated Dec. 15, 2014 (English version).
United States Office Action dated Apr. 14, 2015 in co-pending U.S. Appl. No. 14/033,868.
United States Office Action dated Aug. 26, 2015 in co-pending U.S. Appl. No. 14/033,868.

* cited by examiner

*Primary Examiner* — Nicole Ippolito
*Assistant Examiner* — Hanway Chang
(74) *Attorney, Agent, or Firm* — McGinn IP Law Group PLLC

(57) ABSTRACT

A press plate includes: a press section that is disposed to face towards an imaging face of an imaging table and is resiliently deformable; and a reaction force section that is capable of supporting the press section from the opposite side to the imaging face, that has a variable support force, and that adjusts the reaction force arising in the press section by changing the support force to the press section. The press plate may further includes a reaction force adjustment mechanism that changes the support force of the reaction force section.

16 Claims, 14 Drawing Sheets

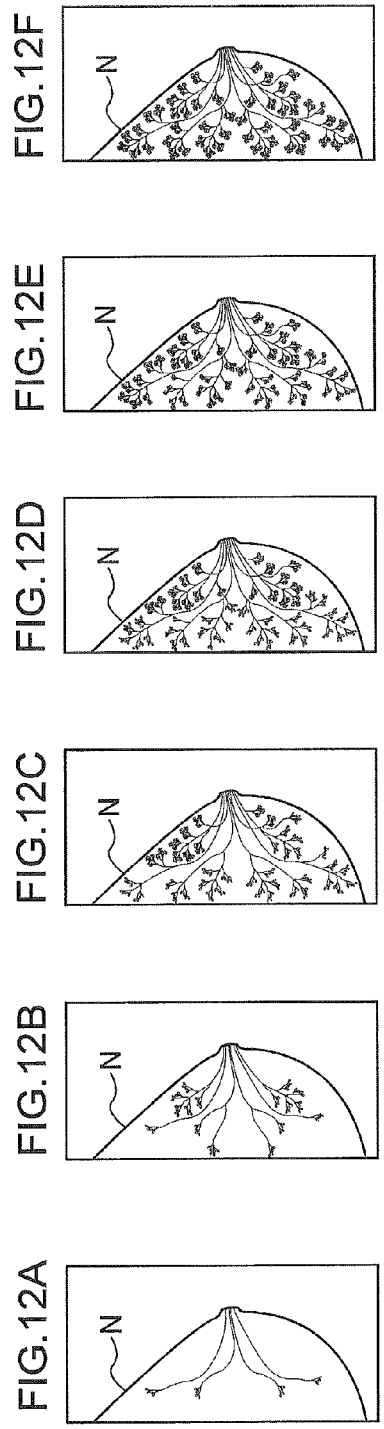
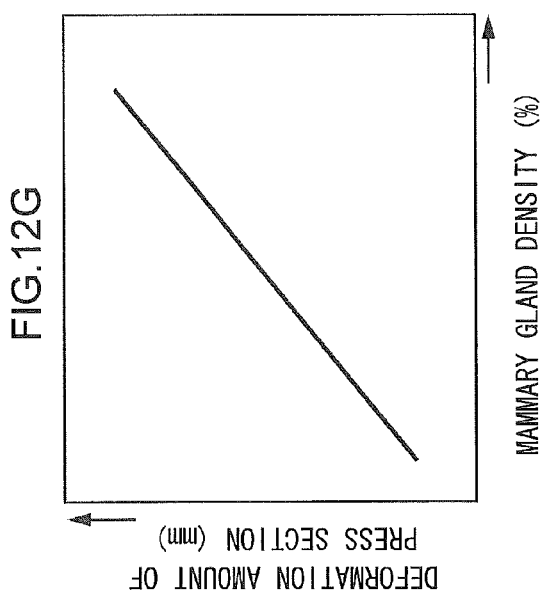

PRESS PLATE AND RADIOGRAPHIC IMAGING APPARATUS

CROSS-REFERENCE TO RELATED APPLICATION

This application claims priority under 35 USC 119 from Japanese Patent Application No. 2012-218265 filed on Sep. 28, 2012, the disclosure of which is incorporated by reference herein.

BACKGROUND OF THE INVENTION

1. Technical Field

The present invention relates to a press plate and a radiographic imaging apparatus, and in particular to a press plate for performing image capture with an image capture body in a compressed state, and to a radiographic imaging apparatus provided with such a press plate.

2. Related Art

Mammography equipment for early detection of breast cancer and the like are known as medical radiographic imaging apparatuses. In mammography equipment, the breast of an examinee is interposed as an image capture body between an imaging face of an imaging table and a press plate, and then a radiographic image is captured with the breast in a pressed state by the press plate. Adopting such an imaging method makes the thickness of the image capture body thinner, and so enables a clear radiographic image to be obtained and enables the radiation amount to be reduced.

In Japanese Patent Application Laid-Open (JP-A) No. 2011-206438, a radiographic imaging apparatus and a press plate for a radiographic imaging apparatus are described that enable the burden on an examinee during breast pressing, and in particular the pain felt by the examinee, to be reduced. The press plate is equipped with a flexible press plate section that presses the breast against the imaging face of an imaging table, a reinforcement plate section that is integrally formed at both ends of the press plate section, and a support plate section that spans across the reinforcement plate section and maintains a gap to the press plate section.

SUMMARY

According to an aspect of the present disclosure, a press plate includes: a press section that is disposed to face towards an imaging face of an imaging table and is resiliently deformable; and a reaction force section that is capable of supporting the press section from the opposite side to the imaging face, that has a variable support force, and that adjusts the reaction force arising in the press section by changing the support force to the press section.

BRIEF DESCRIPTION OF THE DRAWINGS

Exemplary embodiments of the present invention will be described in detail based on the following figures, wherein:

FIG. 12A, FIG. 12B, FIG. 12C, FIG. 12D, FIG. 12E, and FIG. 12F are illustrations schematically illustrating images captured of a breast from the side for adjusting a deformation amount of a press section of a press plate in a radiographic imaging apparatus according to the second exemplary embodiment;

FIG. 12G is a graph illustrating a relationship between mammary gland density and press section deformation amount;

DETAILED DESCRIPTION OF THE INVENTION

Figure 1:
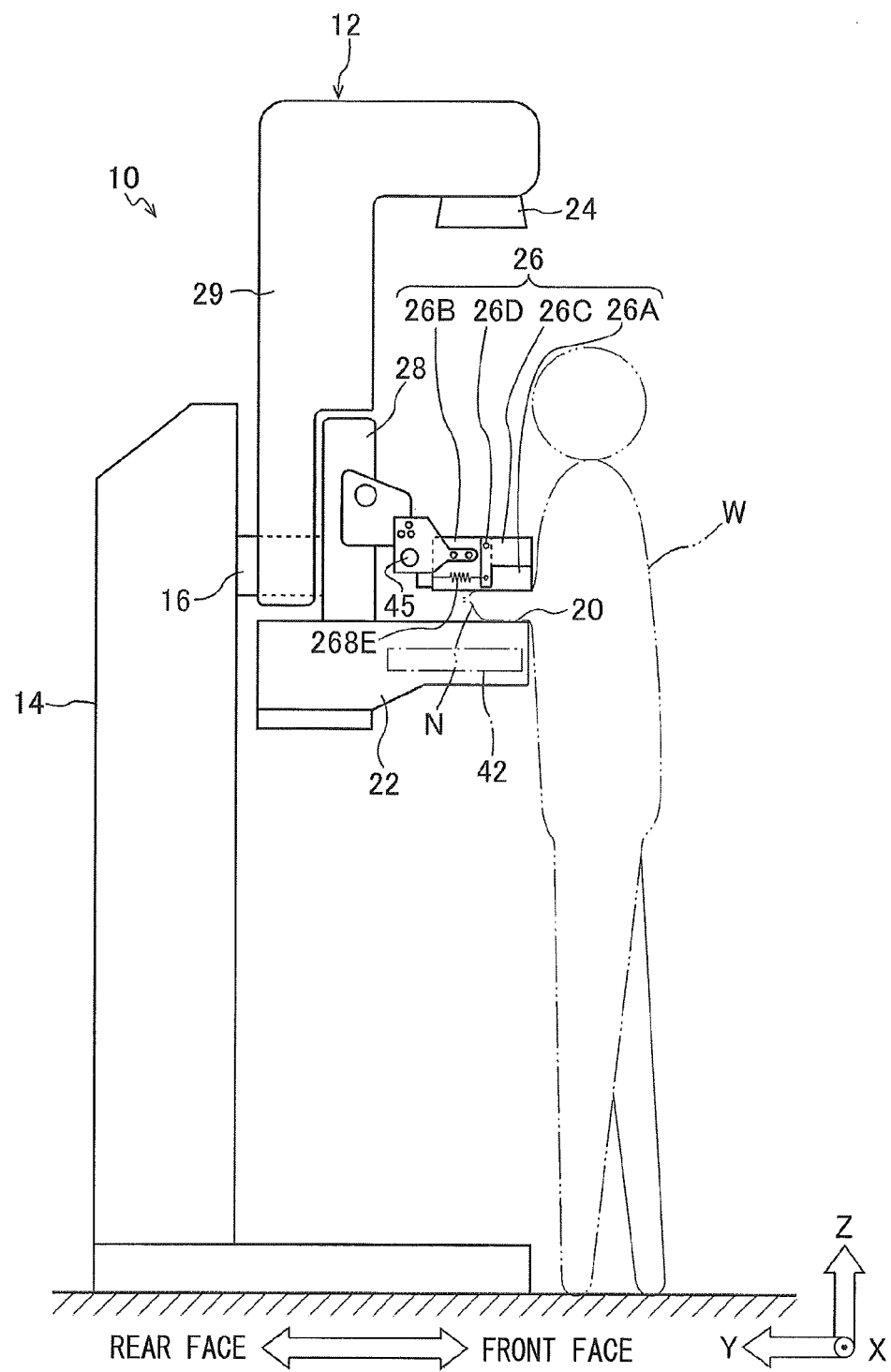
FIG. 1 is a schematic side view illustrating an overall configuration of a radiographic imaging apparatus according to a first exemplary embodiment of the present invention.

Explanation follows regarding exemplary embodiments of the present invention, with reference to the attached drawings. Note that configuration elements having similar functions are allocated the same reference numerals in the drawings, and duplicated explanation thereof is omitted as appropriate. As appropriate, the direction denoted by X in the drawings illustrates the direction from the right side towards the left side as viewed by an examinee (imaging subject) who is in a state oriented facing towards a radiographic imaging apparatus for radiographic imaging. Similarly, the direction denoted by Y in the drawings illustrates the direction from the front side of the examinee towards the rear face of the radiographic imaging apparatus, and the direction denoted by Z in the drawings illustrates the direction from the side below the feet of the examinee towards the upper side of the radiographic imaging apparatus.

First Exemplary Embodiment

In a first exemplary embodiment of the present invention, an example will be explained in which the present invention is applied to mammography equipment as a radiographic imaging apparatus, and to a press plate incorporated therein.

Overall Configuration of Radiographic Imaging Apparatus

As illustrated in FIG. 1, the radiographic imaging apparatus 10 according to the first exemplary embodiment is mammography equipment. The radiographic imaging apparatus 10 is configured to capture an image of a breast (image capture body) N of an examinee W using radiation while the examinee W is in an upright state. Note that the radiographic imaging apparatus 10 is capable of separately imaging the left and right breasts N of the examinee W who is in a seated state on a seat such as a wheelchair, wherein only the upper body of the examinee W is in an upright state.

The radiographic imaging apparatus 10 is equipped with an imaging section 12 that is substantially C-shaped in side view and is provided at a front face (examinee W) side, and a base section 14 that is disposed further towards the Y direction (rear face) side than the imaging section 12 and supports the imaging section 12 from the rear face. The imaging section 12 is equipped from the lower side to the upper side with: an imaging table 22; a holder 28; a press plate 26; and a support section 29. The imaging table 22 is equipped with an imaging face 20 that makes contact with the breast N of the examinee W. In this case the shape of the imaging face 20 is rectangular in plan view, although there is no particular limitation to the shape thereof. From the perspectives of radiation permeability and mechanical strength, at least the imaging face 20 is formed from for example a carbon fiber reinforced plastic. The imaging table 22 is supported at the lower side of the holder 28, and the press plate 26 is supported by the holder 28 further to the upper side than the imaging table 22.

The press plate 26 is configured to interpose the breast N between itself and the imaging face 20, and to compress the breast N. The shape of the press plate 26 is rectangular-shaped in plan view, and is configured such as a rectangular box shape with thickness along the Z direction. The press plate 26 is configured movable in the vertical direction with respect to the imaging face 20 (the Z direction in FIG. 1) so as to compress the breast N in a parallel state with respect to the imaging face 20. The press plate 26 is also configured rotatable about rotation supports points 45 provided between the press plate 26 and the holder 28, so as to be capable of compressing the breast N while supported at an angle with respect to the imaging face 20 (capable of tilted compressing). Namely, pain felt by the examinee W can be reduced during breast N compression due to the press plate 26 being held tilted about the rotation supports points 45 so as to widen out towards the base side of the breast N. Although not illustrated in the drawings, an angle detection sensor is provided at the rotation supports points 45, or in the vicinity thereof, to detect the compression tilt angle. Note that a detailed explanation regarding the construction of the press plate 26 and regarding the operation of the press plate 26 is given later.

The support section 29 is provided above the holder 28 as a separate component to the holder 28 and is configured shaped in a substantially inverted L-shape in side view. A radiation irradiation section 24 is provided at the upper side of the support section 29, facing towards the imaging face 20, and capable of irradiating radiation for imaging or for measurement.

As illustrated in FIG. 1, a rotation shaft 16 is provided at the upper side of the base section 14 so as to project out in a horizontal direction towards the apparatus front face side, and the support section 29 and the holder 28 are attached to the rotation shaft 16. Namely, the imaging section 12, including the support section 29, is rotatable with respect to the base section 14 about the rotation shaft 16.

It is also possible to switch between the coupled state of the rotation shaft 16 and the holder 28 together, or the uncoupled state of the rotation shaft 16 and the holder 28. In order to incarnate the such switching, for example, a gear wheel is provided to the rotation shaft 16 and the holder 28 that is switchable between a meshed state and an unmeshed state. In the coupled state, the holder 28 rotates accompanying rotation of the rotation shaft 16, and in the uncoupled state, the holder 28 is free to rotate with respect to rotation of the rotation shaft 16. The rotational force of the rotation shaft 16 is transmitted from a drive source provided inside the base section 14, not illustrated in the drawings.

Configuration of Radiation Irradiation Section

Figure 2:
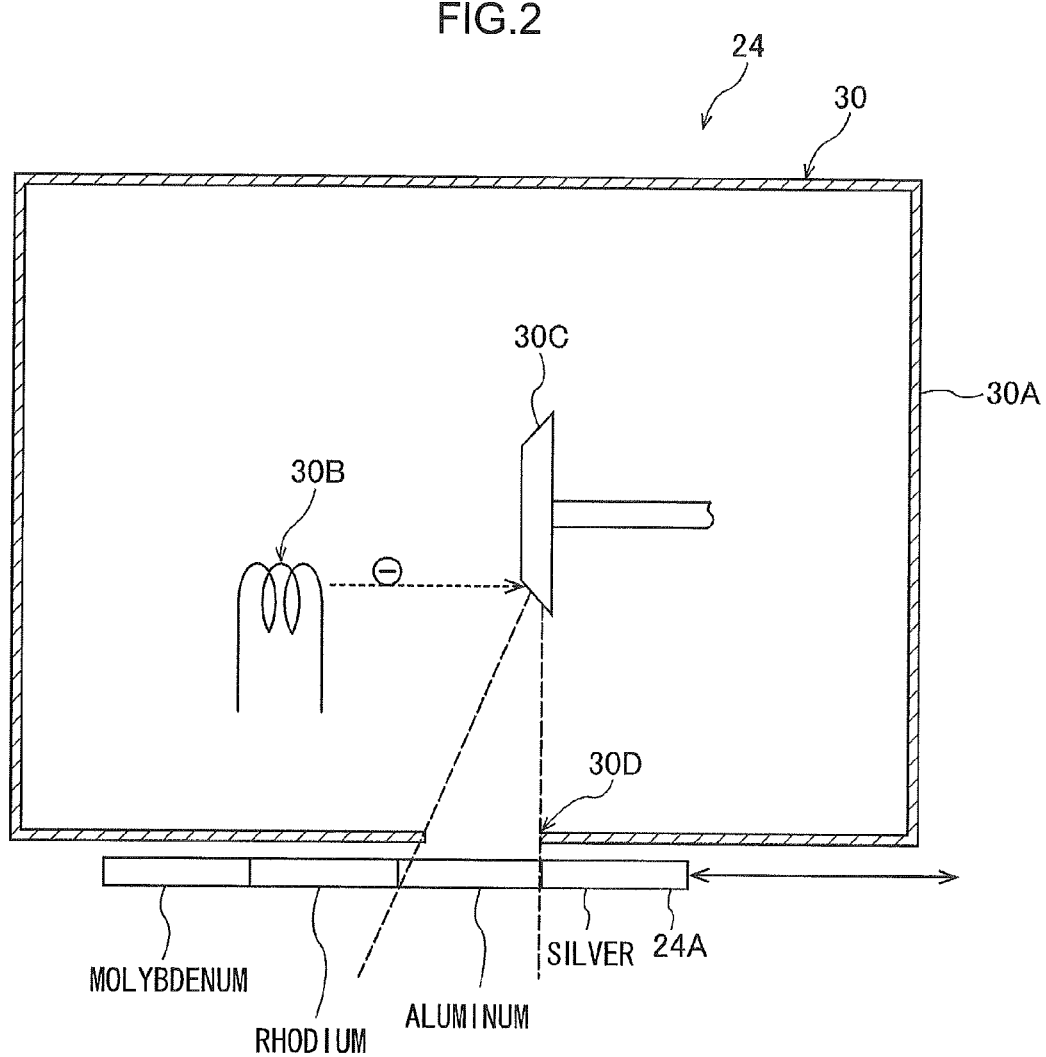
FIG. 2 is a schematic cross-section of a radiation irradiation section of the radiographic imaging apparatus illustrated in FIG. 1.

As illustrated in FIG. 2, the radiation irradiation section 24 is equipped with a radiation source 30 and a filter 24A. The radiation source 30 is equipped with a casing 30A, and is internally provided therein with a cathode 30B including a filament and an anode 30C used as a target. Thermions are emitted from the cathode 30B, the thermions are accelerated by the potential difference between the cathode 30B and the anode 30C, and are focused on and impact with the anode 30C. Bremsstrahlung is generated thereby. In the present case bremsstrahlung X-rays are emitted from the radiation irradiation section 24. Although not illustrated in the drawings, in the radiographic imaging apparatus 10 according to the first exemplary embodiment, there are plural individual radiation sources 30 provided, with different types of metal employed as the anode 30C for each of the plural individual radiation sources 30. Examples of metals that may be employed as the anode 30C include tungsten, molybdenum, and rhodium. The intensity of the bremsstrahlung emitted from the anode 30C differs according to the different types of metal.

Bremsstrahlung emitted from the radiation source 30 (sometimes simply referred to below as "radiation") passes through a window 30D provided in a lower wall (in this case a bottom section) of the casing 30A, then passes through the filter 24A provided at the outside of the window 30D, and is irradiated towards the imaging face 20. The filter 24A is, for example, a structure in which films of molybdenum, rhodium, aluminum and silver are joined sequentially along their film face direction. In the radiographic imaging apparatus 10 according to the first exemplary embodiment, the filter 24A is configured so as to be movable, for example, along the guide rail, not illustrated in the drawings, such that one of the metals of the filter 24A is disposed facing towards the window 30D. Namely, the radiation emitted from the window 30D passes through the changeable metal of the filter 24A, so as to enable irradiation towards the imaging face 20, enabling the characteristics of the radiation to be changed as appropriate.

Configuration of Radiation Detector

As illustrated in FIG. 1, a radiation detector 42 is internally provided to the imaging table 22. In the radiation detector 42, irradiated radiation from the radiation irradiation section 24, that has passed through the press plate 26, the breast N and the imaging face 20, and has picked up image data of the breast N, is received and the image data is detected. This image data is output to a storage section 47 (see FIG. 4), and stored as radiographic image data of the breast N in the storage section 47. A Flat Panel Detector (FPD) that converts radiation into a digital signal, for example, is employed as the radiation detector 42.

In the radiation detector 42 according to the first exemplary embodiment, an indirect-conversion-type detector is employed in which radiation is first converted into light using a scintillator, not illustrated in the drawings, and then the converted light is converted into charges. Note that there is no limitation to an indirect-conversion-type detector, and a direct-conversion-type detector may be employed for the radiation detector 42, in which radiation is directly converted into charges in a semiconductor layer and the charges are accumulated.

Figure 3:
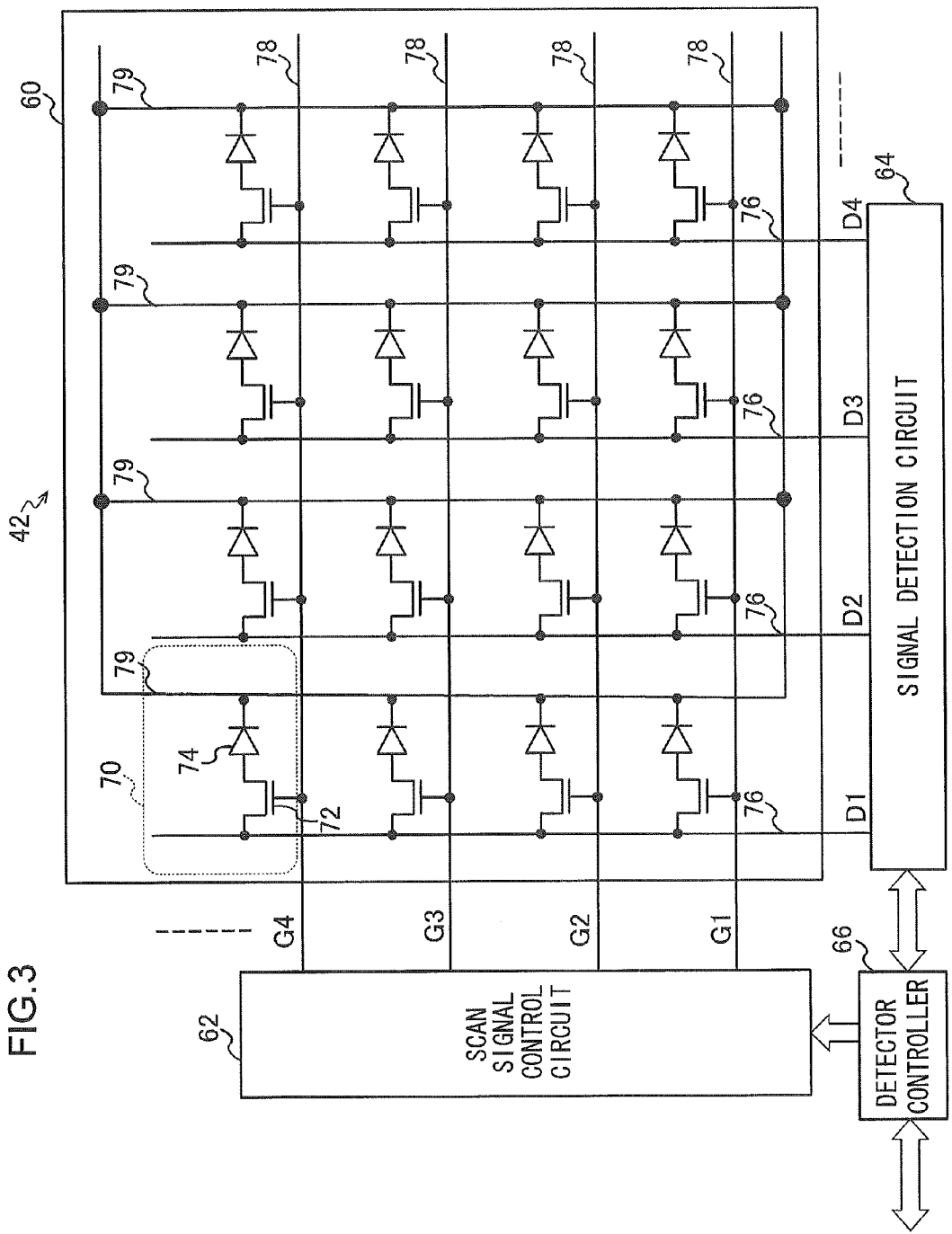
FIG. 3 is a block circuit diagram of a radiation detector of the radiographic imaging apparatus illustrated in FIG. 1.

As illustrated in FIG. 3, the radiation detector 42 has a detection section 60 with plural individual detection elements (pixels) 70 arrayed. Each of the detection elements 70 has a serial circuit of a photoelectric conversion portion 74 that generates charges on receipt of light converted from radiation and accumulate the charges, and a switching element 72 that reads out the charges accumulated in the photoelectric conversion portion 74. A photodiode may, for example, be employed as the photoelectric conversion portion 74. A Thin Film Transistor (TFT) is employed as the switching element 72.

Plurality of the detection elements 70 are arrayed, in a matrix form, along a direction of extension of scan signal lines 78 (for example a row direction), and along a direction of extension of output signal lines 76 that intersect with the scan signal lines 78 (for example a column direction). The scan signal lines 78 and the output signal lines 76 are provided on a substrate, not illustrated in the drawings. Each individual detection element 70 is disposed on the substrate at an intersection portion of one of the scan signal lines 78 and one of the output signal lines 76, and is electrically connected respectively to the one scan signal line 78 and the one output signal line 76. The detection section 60 illustrated in FIG. 3 is simplified to suit the page area, and is arrayed with several individual detection elements 70, however in practice there may be, for example, 1024 individual detection elements 70 arrayed in the scan signal line 78 extension direction and 1024 individual detection elements 70 arrayed in the output signal line 76 extension direction.

Moreover, in the detection section 60 there are also plural common electrode lines 79, each of which is provided so as to extend parallel to the output signal lines 76, respectively. A fixed power supply is supplied to the common electrode lines 79, and the common electrode lines 79 are connected to the corresponding photoelectric conversion portions 74.

A scan signal control circuit 62 is connected to the scan signal lines 78, enabling scan signals from the scan signal control circuit 62 to be supplied to the scan signal lines 78. The switching element 72 of each of the detection elements 70 connected to each of the scan signal lines 78 is controlled to a conducting or non-conducting state in response to the supply, or the non-supply, of respective scan signals. In the detection elements 70, the current flows in the switching element 72 according to the charge amount accumulated in the photoelectric conversion portion 74 at times when the switching element 72 is controlled to the conducting state. The charge amount, and the current amount flowing according to the charge amount, is radiographic image data of the breast N.

A signal detection circuit 64 is connected to the output signal lines 76. The current flowing in the switching element 72 of each of the detection elements 70 is output, as an output electrical signal of the detection element 70, through the output signal lines 76 to the signal detection circuit 64. Amplifiers to amplify the output electrical signals and AD converters to convert analogue signals into digital signals, not illustrated in the drawings, are built in the signal detection circuit 64 for each of the output signal lines 76. Namely, in the signal detection circuit 64, the output electrical signals (analogue signals) input from the output signal lines 76 are amplified by the amplification circuits, and converted to digital signals by the AD converters.

A detector controller 66 is provided in the radiation detector 42, and the detector controller 66 is connected both to the scan signal control circuit 62 and to the signal detection circuit 64. In the detector controller 66, specific processing such as noise reduction is performed on the digital signals output form the signal detection circuit 64, and a control signal to control detection of output electrical signals is output to the signal detection circuit 64. In the detector controller 66, a control signal to control output of scan signals is also output to the scan signal control circuit 62. The detector controller 66 is equipped with a Central Processing Unit (CPU), Read Only Memory (ROM), Random Access Memory (RAM), and a non-volatile storage section such as flash memory. In the detector controller 66, image data that is a radiographic image of the breast N is generated based on the output electrical signals of the detection elements 70 output from the signal detection circuit 64, and this image data is output to the storage section 47 (see FIG. 4) of the radiographic imaging apparatus 10.

Note that, in the radiation detector 42 illustrated in FIG. 3, one scan signal control circuit 62 and one signal detection circuit 64 is provided for the individual detection section 60. The scan signal control circuit 62 and the signal detection circuit 64 are however not limited to such a configuration, and two or more scan signal control circuits 62 and two or more signal detection circuits 64 may be provided for the detection section 60.

System Configuration of Radiographic Imaging Apparatus

Figure 4:
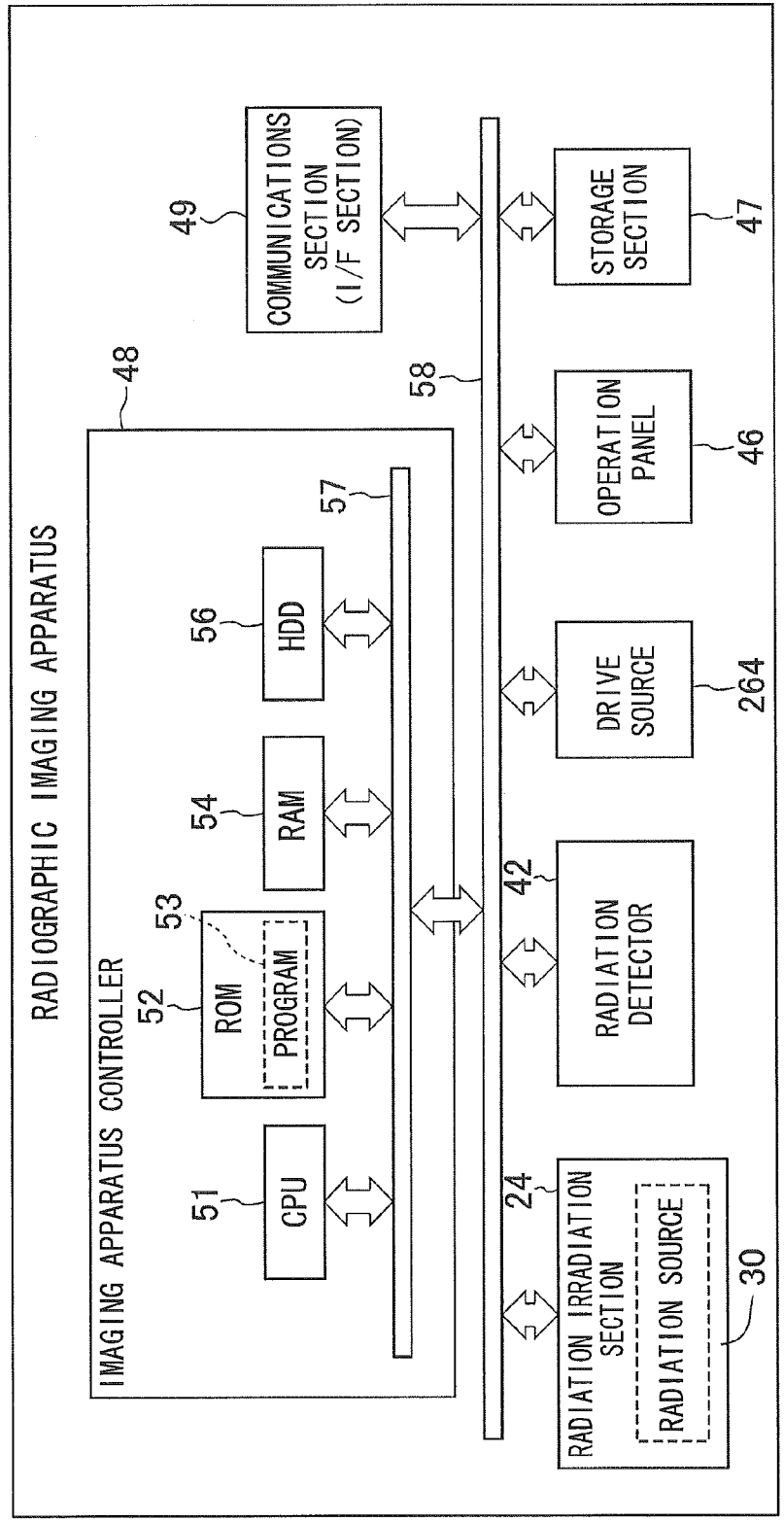
FIG. 4 is an overall system block diagram of the radiographic imaging apparatus illustrated in FIG. 1.

As illustrated in FIG. 4, the radiographic imaging apparatus 10 according to the first exemplary embodiment is equipped with an imaging apparatus controller 48, the radiation irradiation section 24, the radiation detector 42, an operation panel 46, the storage section 47, a communications section (I/F section) 49 and a drive source 264.

The imaging apparatus controller 48 is equipped with a CPU 51, ROM 52, RAM 54, and a Hard Disk Drive (HDD) 56. The CPU 51 and other sections are connected together by a common bus 57 such as a control bus or a data bus, thereby enabling transmission and reception of signals and the like between one another.

The CPU 51 performs overall control of the radiographic imaging apparatus 10. For example, when the CPU 51 has read in a program 53 stored on the ROM 52, the CPU 51 performs control of each section to implement the program 53. Note that although a configuration is given here in which the program 53 is pre-stored on ROM 52 there is no limitation thereto. For example, an external recording medium such as a CDROM or a removable device in which the program 53 is stored may be created, and then the program 53 may be installed from the external recording medium onto for example the ROM 52. Moreover, the program 53 may be installed from an external device via a communication line such as the internet onto the ROM 52 for example. The RAM 54 is employed as work space during execution of the program 53 by the CPU 51, and the program 53 is temporarily stored on the RAM 54. Various data such as radiographic image data is stored in the HDD 56. In the imaging apparatus controller 48, the radiation irradiation section 24, the radiation detector 42, the operation panel 46, the storage section 47, the communications section (I/F section) 49 and the drive source 264 are connected to one another through the internally provided common bus 57 and an externally provided common bus 58.

In the radiographic imaging apparatus 10, a radiation irradiation instruction is generated on operation of an exposure switch of the operation panel 46 by a user (operator). Following the radiation irradiation instruction, the imaging apparatus controller 48 executes an imaging procedure (the program 53) set based on the instructed exposure conditions, and the control of the irradiation of the radiation from the radiation irradiation section 24 towards the imaging face 20 is performed.

The operation panel 46 is an interface between the radiographic imaging apparatus 10 and the operator, is capable of performing for example input of various operation data such as exposure conditions and orientation data, and is capable of setting various operation instructions. Exposure conditions include at least data such as tube voltage, tube current, exposure time, and orientation data. For cases in which image capture is performed from plural directions with respect to the breast N, the orientation data includes at least data of imaging orientation and imaging position data such as imaging angle data. Note that the various operation data and various operation instruction data may be acquired from an external device or system, such as a system that manages data related to radiation-based medical consultation and radiation-based diagnosis, which is referred to as a Radiology Information System (RIS). Moreover, various operation data and various operation instruction data may be pre-stored on the HDD 56 of the imaging apparatus controller 48.

In the imaging apparatus controller 48, on input of the various operation data and the various operation setting instructions from the operation panel 46, an imaging procedure is executed based on the settings, radiation from the radiation irradiation section 24 is irradiated onto the breast N of the examinee W and a radiographic image is captured. In cases in which a radiographic image of the breast N is captured from above, the orientation of the holder 28 is adjusted such that the imaging face 20 is in an upwards facing state, and the orientation of the support section 29 is adjusted such that the radiation irradiation section 24 is positioned above and facing towards the imaging face 20. Moreover, in cases in which a radiographic image of the breast N is captured from the side, the orientation of the holder 28 is adjusted such that the imaging face 20 is in state facing towards the side, and the orientation of the support section 29 is adjusted such that the radiation irradiation section 24 is positioned to the side and faces towards the imaging face 20. Such an adjustment is performed by the imaging apparatus controller 48.

The communications section 49 is employed as an interface that transmits radiographic image data stored for example in the storage section 47 of the radiographic imaging apparatus 10 to an external device (for example an external monitor), or receives data such as various operation data from an external device (for example RIS) or various operation instructions. In the communications section 49, there is no limitation to transmitting and receiving of data by wired technology and data may be transmitted and received using wireless technology.

Configuration of Press Plate

Figure 5:
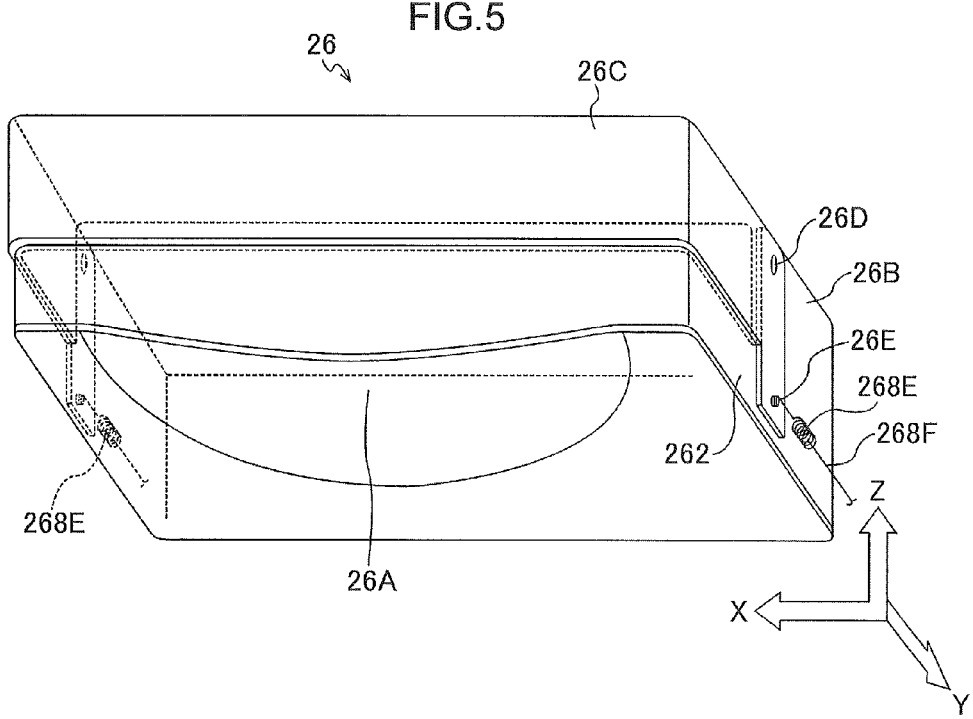
FIG. 5 is a perspective view from the front-face side of a press plate of the radiographic imaging apparatus illustrated in FIG. 1.
Figure 6:
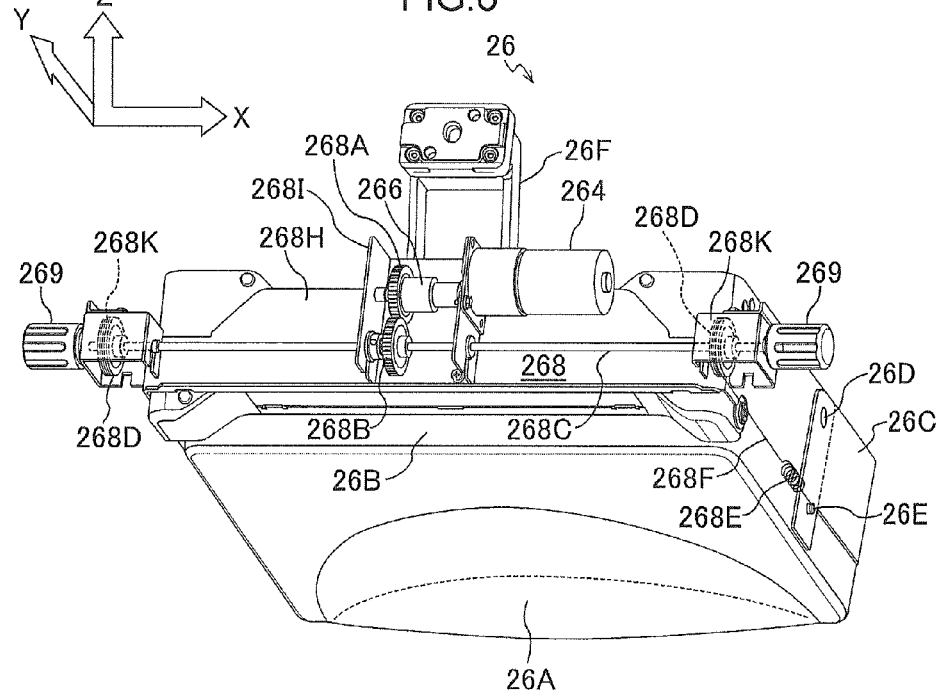
FIG. 6 is a perspective view from the back-face side of the press plate illustrated in FIG. 5.

As illustrated in FIG. 5 and FIG. 6, the press plate 26 incorporated in the radiographic imaging apparatus 10 according to the first exemplary embodiment has a hollow rectangular box shape and is equipped with at least a press section 26A, a support section 26B, and a reaction force section 26C. The press section 26A is disposed facing towards the imaging face 20 of the imaging table 22, has a thickness in the Z direction that is thinner than the thickness of support section 26B and is configured more elastically deformable than the support section 26B. The press section 26A is positioned at the chest wall side of the examinee W, and is configured in a rectangular shape having a long-side direction along the X direction in plan view. The support section 26B is, similarly to the press section 26A, disposed facing towards the imaging face 20, and is integrally provided at one end of the back-face side of the press section 26A. Namely, the press section 26A and the support section 26B are formed from the same member, the front-face side of the member with the thickness thinner forming the press section 26A and the remaining section of the member forming the support section 26B. The support section 26B is configured with a rectangular shape in plan view, and the press section 26A and the support section 26B configure a substantially L shape as viewed from the side face. The overall rigidity of the support section 26B is high due to the support section 26B being formed thick. In contrast thereto, the overall rigidity of the press section 26A is low due to the press section 26A being formed thin, thereby making the press section 26A deformable.

The press section 26A and the support section 26B of the press plate 26 are formed using a resin material with properties that allow easy transmission of the bremsstrahlung X-rays used here as the radiation. More specific examples of materials that may be employed as such resin materials include polycarbonate (PC), polyethylene terephthalate (PET), acrylates, and polypropylene (PP).

Figure 7A:
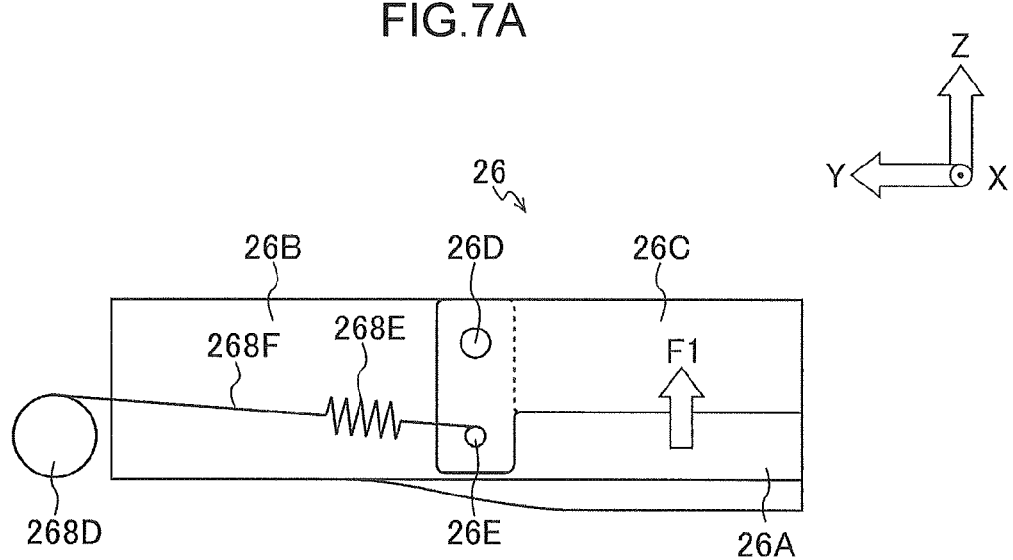
FIG. 7A is a schematic side view of the press plate illustrated in FIG. 5 and FIG. 6 in a state in which support force is not biased to the press section.

As illustrated in FIG. 5, FIG. 6 and FIG. 7A, the one end portion of the reaction force section 26C, which is the front end side portion, is supportable for the press section 26A at the opposite side of the press section 26A to the imaging face 20 (in the Z direction, in FIG. 5 and FIG. 6). Another end portion that is at the back-face side of the reaction force section 26C extends downwards from the one end portion and is connected to the reaction force adjustment mechanism 268. The reaction force section 26C is formed in a substantially L-shape in side view. An intermediate portion of the reaction force section 26C is attached to the support section 26B through a rotation shaft 26D, such that the reaction force section 26C is rotatable about the rotation shaft 26D. The reaction force section 26C is basically configured from a material having a greater coefficient of elasticity than the coefficient of elasticity of the press section 26A in order to bias the support force. The reaction force section 26C may for example be manufactured from a metal. Variation occurs in the reaction force received by the press section 26A due to the reaction force section 26C having capability to vary the support force for biasing the press section 26A using the reaction force adjustment mechanism 268.

Figure 7B:
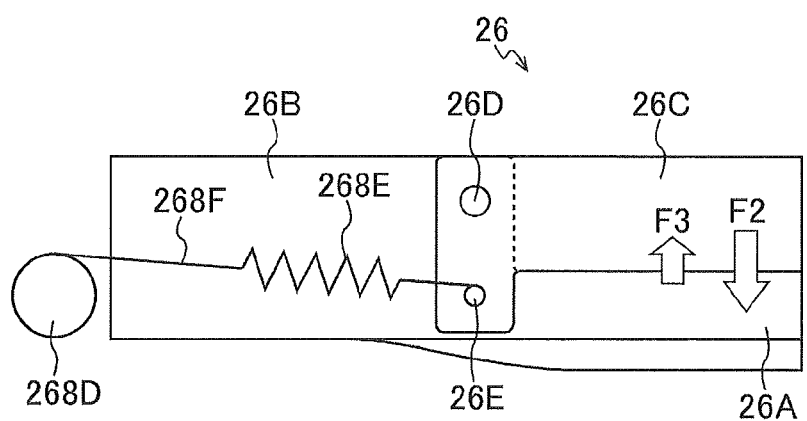
FIG. 7B is a schematic diagram of the press plate illustrated in FIG. 5 and FIG. 6 in a state in which support force is biased to the press section.

As illustrated in FIG. 7A, when there is no support force to the press section 26A from the reaction force section 26C, the press section 26A undergoes resilient deformation according to the coefficient of elasticity in response to a reaction force F1 that arises when the breast N is being squashed. In such cases the press plate has a low rigidity and there is a large resilient deformation of the press section 26A. In contrast thereto, as illustrated in FIG. 7B, in cases in which a support force F2 biases (or is large) from the reaction force section 26C to the press section 26A, the reaction force F1 arising when the breast N is being squashed by the support force F2 is reduced to reaction force F3. In such cases the press plate has a high rigidity and there is a small resilient deformation of the press section 26A. Namely, the deformation amount of the press section 26A is adjustable due to being able to change the shape (cross-sectional shape) of the press section 26A by changing the reaction force. This consequently also enables the rigidity of the press plate to be changed.

As illustrated in FIG. 5, FIG. 6, FIG. 7A and FIG. 7B, one portion that is located at the front-face side of the press section 26A is configured with a local surface profile that projects out to the imaging face 20 side. Specifically, this portion of the press section 26A, has a circular arc shape in plan view, similar to the shape of the breast N, that widens out towards the front-face side and gradually narrows on progression towards the back-face side, with the projection amount decreases progressively from the front-face side towards the back-face side. Consequently, when the breast (image capture body) N, that is softer than the press section 26A and that has a local surface profile that projects out towards the press section 26A side, is interposed between the imaging face 20 and the press section 26A, a central portion of the breast N is pressed by the local surface profile of the press section 26A and the vicinity of the central portion is spread out. The thickness of the breast N interposed between the imaging face 20 and the press section 26A can thereby be made uniform. In the first exemplary embodiment, the press section 26A is configured such that the thickness of the breast N is made uniform by the local surface profile within a practical range of pressing force of 40N to 120N.

Configuration of the Reaction Force Adjustment Mechanism of the Press Plate

As illustrated in FIG. 5, FIG. 6, FIG. 7A, FIG. 7B and FIG. 8, the reaction force adjustment mechanism 268 of the press plate 26 of the first exemplary embodiment is equipped with resilient bodies 268E each of which is connected to one end of the reaction force section 26C and biases the support force to the reaction force section 26C, and an adjustment section (not allocated a reference numeral) which is connected to the other end of each of the resilient bodies 268E and adjusts the extension/contraction of the resilient bodies 268E. A coil spring may, for example, be employed for each of the resilient bodies 268E. One end of each of the resilient bodies 268E is attached to the reaction force section 26C through a coupling pin 26E.

The adjustment section is equipped with coupling lines 268F that are connected to the other end of the resilient bodies 268E, reels 268D that roll up and let out the coupling lines 268F, a drive source 264 that generates drive force on the reels 268D for rolling up or letting out, and a transmission section that couples together the drive source 264 and each of the reels 268D and transmits the drive force from the drive source 264 to the reels 268D. Wire may, for example, be employed for each of the coupling lines 268F. The transmission section is configured by a gear wheel 268A, a gear wheel 268B and a rotation transmission shaft 268C.

An electrical motor may, for example, be employed as the drive source 264. Here, the direction of the rotation shaft (drive shaft) of the electrical motor is aligned with the X direction. The drive source 264 is attached to the support section 26B through a plate-shaped bracket 268H that is attached to a rear face of the support section 26B, and through a plan view U-shaped bracket 268I that is attached to a central portion of the bracket 268H and that is open towards the outside.

Figure 8:
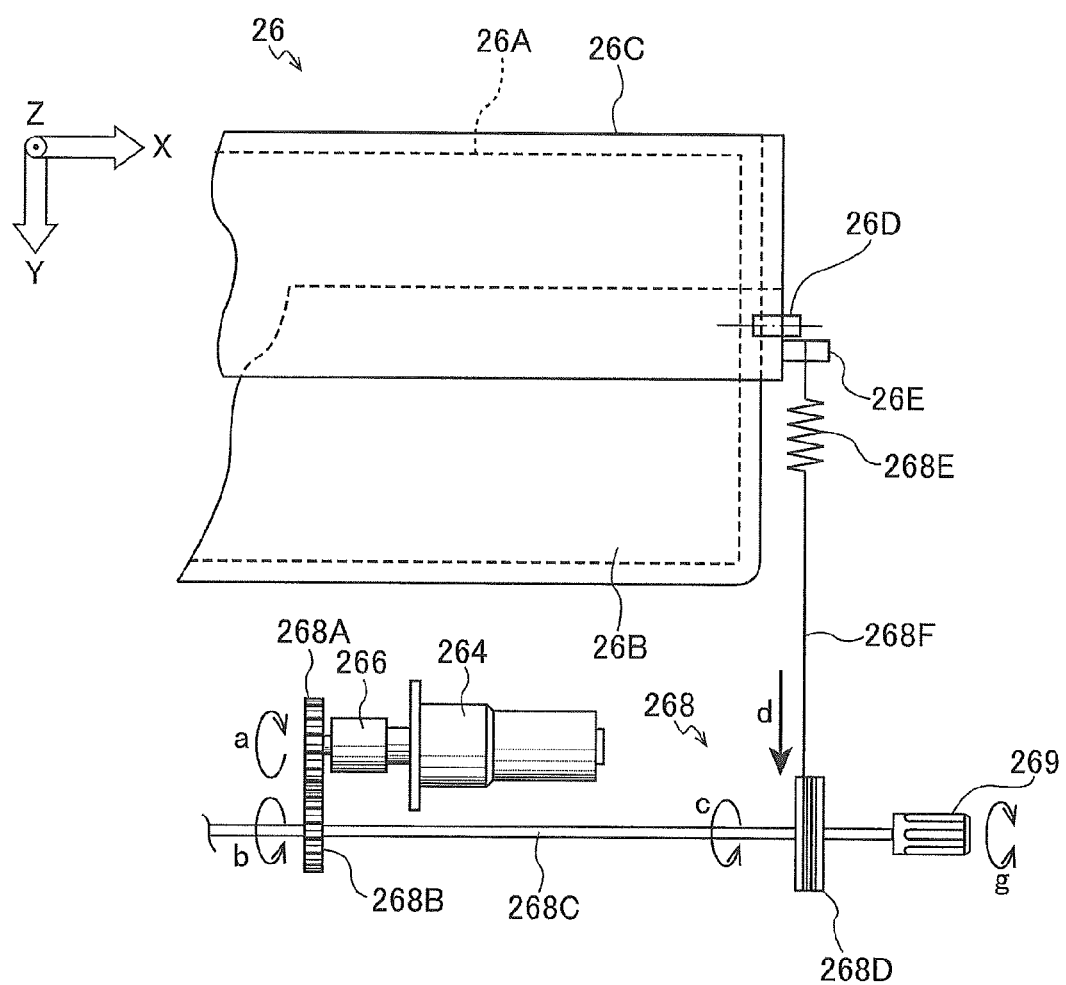
FIG. 8 is a schematic plan view of part of a reaction force adjustment mechanism of the press plate illustrated in FIG. 6, in plan view.

The gear wheel 268A of the transmission section is rotatably attached to the bracket 268I, and receives drive force from the drive source 264. A clutch 266 is provided between the drive source 264 and the gear wheel 268A, with the clutch 266 enabling switching between a state in which drive force from the drive source 264 is transmitted to the gear wheel 268A, and a state in which drive force is not transmitted thereto. The gear wheel 268B is similarly rotatably attached to the bracket 268I, and rotates on receipt of drive force transmitted from the gear wheel 268A. The rotation transmission shaft 268C is connected to the rotation shaft of the gear wheel 268B, and is rotatably attached to brackets 268K, so as to rotate on receipt of drive force transmitted from the gear wheel 268B. The rotation transmission shaft 268C extends at the rear face of the press plate 26 in the X direction so as to span across between both side faces of the press plate 26, and a central portion of the rotation transmission shaft 268C is connected to the gear wheel 268B. The reels 268D are connected to the two ends of the rotation transmission shaft 268C, and the reels 268D rotate on receipt of drive force transmitted from the rotation transmission shaft 268C. As illustrated in FIG. 8, when drive force (rotation) is transmitted for example, in the a-arrow rotation direction, from the drive source 264 to the gear wheel 268A, the drive force is transmitted to the gear wheel 268B in the b-arrow rotation direction that is opposite to the a-arrow rotation direction. The drive force shown in the b-arrow rotation direction is transmitted through the rotation transmission shaft 268C to the reels 268D as the drive force shown in the c-arrow rotation direction that is the same as the b-arrow rotation direction.

An extension of the resilient bodies 268E occurs when, as illustrated in FIG. 7B, the reels 268D rotate in the c-arrow rotation direction and the coupling lines 268F are rolled up on the reels 268D, thereby increasing the support force F2 from the reaction force section 26C with respect to the press section 26A. The support force increases according to the increase in the extension of the resilient bodies 268E. Contrarily, the resilient bodies 268E shrinks when, as illustrated in FIG. 7A, the reels 268D are rotated in the opposite rotation direction and the coupling lines 268F from the reels 268D are rolled back thereon, thereby decreasing the support force F2 from the reaction force section 26C with respect to the press section 26A.

Moreover, as illustrated in FIG. 6 and FIG. 8, in the press plate 26 according to the first exemplary embodiment, a manual adjustment section 269 is coupled to the adjustment section of the reaction force adjustment mechanism 268, or more specifically, is respectively coupled to each of the two ends of the rotation transmission shaft 268C. The manual adjustment section 269 imparts drive force to the reels 268D that is separate from the drive force from the drive source 264. In FIG. 8, when a user imparts drive force in the g-arrow rotation direction to the manual adjustment section 269, the reels 268D are rotated according to this drive force. Note that the coupled state between the drive source 264 and the gear wheel 268A is released by the clutch 266 when drive force is imparted from the manual adjustment section 269. The coupled state between the drive source 264 and the gear wheel 268A is released because the drive source 264 would otherwise bear the load when drive force is imparted from the manual adjustment section 269, enabling easy operation of the reels 268D to be performed using the manual adjustment section 269.

Operation of Radiographic Imaging Apparatus and Press Plate

Figure 9:
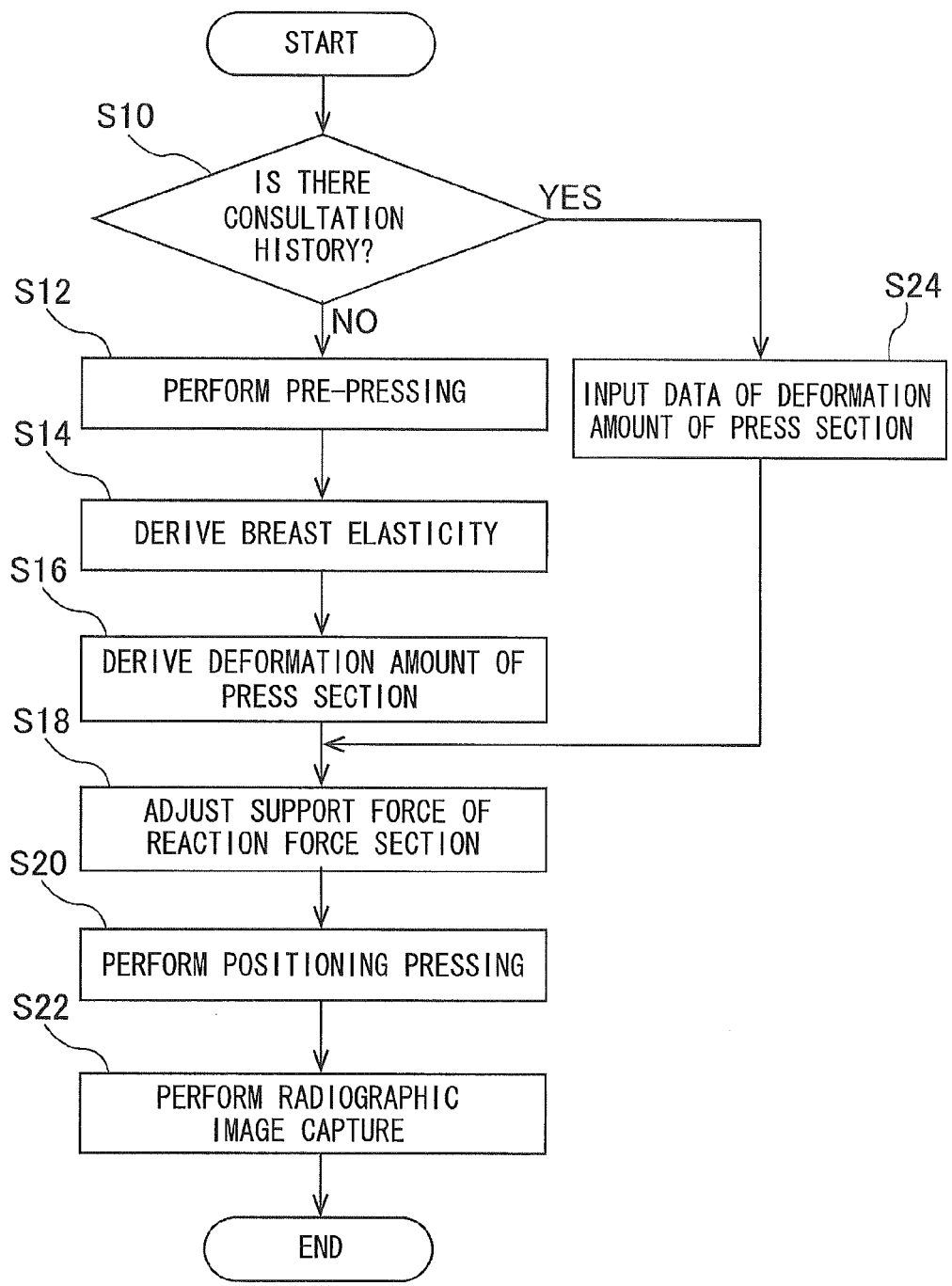
FIG. 9 is a control flow chart of a radiographic imaging apparatus illustrated in FIG. 1.

Operation of the radiographic imaging apparatus 10 and the press plate 26 according to the first exemplary embodiment is as follows. As illustrated in FIG. 9, the first determination is made as to whether or not there is any consultation history for the examinee W (S10). Having a consultation history means that a radiographic image of the breast N has been captured in the past, and that there exists data available for determining a deformation amount of the press section 26A of the press plate 26 during the image capture. It follows that, not having any consultation history means that no such data exists. Determination as to whether or not there is consultation history is executed by the radiographic imaging apparatus 10. Namely, when the data necessary to determine whether or not there exists past consultation history is input from the operation panel 46 illustrated in FIG. 4, the imaging apparatus controller 48 searches past consultation histories stored in the storage section 47. The data necessary to determine refers here to at least one item of, for example, the name, the health insurance number or the patient registration card number of the examinee W. As a result of the search, when there is stored corresponding data in the storage section 47, the imaging apparatus controller 48 determines that there exists consultation history. On the other hand, the imaging apparatus controller 48 determines that there is no consultation history when there is no corresponding data stored in the storage section 47. Note that the determination as to whether or not there is consultation history may be performed also by the interview with the examinee W by a doctor. In such cases, based on the determination result, the doctor or the operator of the radiographic imaging apparatus 10 inputs the determination result through the operation panel 46.

In cases in which there is no consultation history for the examinee W, the pre-pressing of the breast N of the examinee W is performed in the radiographic imaging apparatus 10 (S12). The pre-pressing is pressing performed prior to the positioning pressing during the main radiographic image capture. Specifically, in the pre-pressing the breast N is interposed between the imaging face 20 of the imaging table 22 and the press section 26A of the press plate 26, the breast N is pressed with a light pressing force that does not cause pain to the examinee W, with a pressing force of for example about 60N to 80N.

Figure 10A:
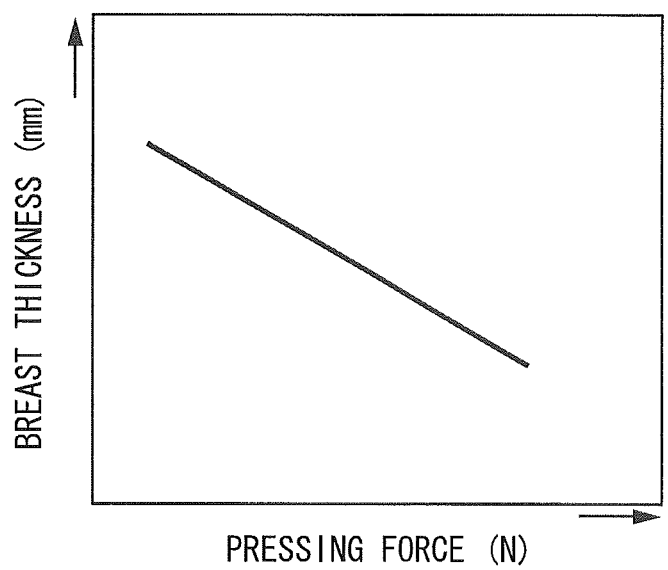
FIG. 10A is a graph illustrating a relationship between pressing force and breast thickness for adjusting the deformation amount of a press section of a press plate in the radiographic imaging apparatus illustrated in FIG. 9.

An example of a relationship between pressing force and thickness of the breast N is illustrated in FIG. 10A. In FIG. 10A, the horizontal axis is pressing force (N) and the vertical axis is the breast N thickness (mm). As illustrated in FIG. 10A, generally the thickness of the breast N tends to become thinner as the pressing force is increased, however there is some difference in this trend due to differences among breasts N of examinees W, one of which is, for example, mammary gland density. In pre-pressing, the thickness of the breast N is measured when the pressing force is applied, and the breast elasticity (N/mm) is derived from the relationship between the applied pressing force and the measured thickness (S14). The breast elasticity is the value which is derived by dividing the pressing force by the thickness. Derivation of the breast elasticity is performed by employing a table that can derive a value for the breast elasticity from the relationships between the values of pressing force and values of thickness of breast N. Such a table is pre-stored in the storage section 47 of the radiographic imaging apparatus 10, as referred to above and illustrated in FIG. 4. Since these values of breast elasticity do not need to be of extremely high precision, it is advantageous for these values to be treated as digital values with a certain width. Namely, the breast elasticity is derived using the table, and as a result it is possible to make the size (for example the computation power) of the system for derivation smaller by using certain width ranges. Moreover, in the imaging apparatus controller 48 illustrated in FIG. 4, configuration may be made such that the program 53 contains a computation formula is pre-stored in the ROM 52, and that the breast elasticity is derived by computation with the CPU 51 on input of the value of the pressing force and the value of the thickness of the breast N through the operation panel 46. Moreover, in the radiographic imaging apparatus 10 illustrated in FIG. 4, a dedicated circuit may be configured to derive breast elasticity. Note that the value of breast elasticity may be derived by fixing one of the pressing force or the thickness of the breast N, and deriving the other value using for example a table.

Figure 10B:
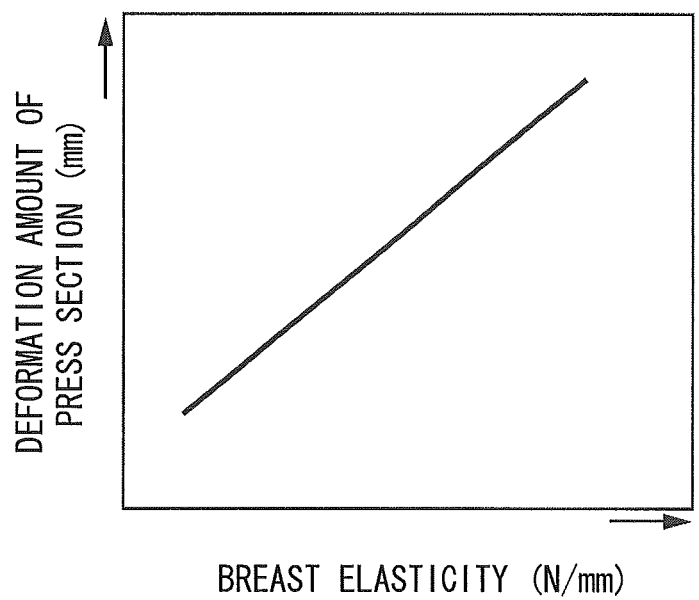
FIG. 10B is a graph illustrating a relationship between breast elasticity and press section deformation amount.

After the derivation of the breast elasticity, a deformation amount of the press plate 26 is, as illustrated in FIG. 10B, derived to the extent that the pain to the examinee W is not liable to arise (S16). In FIG. 10B, the horizontal axis is breast elasticity (N/mm) and the vertical axis is the deformation amount (mm) of the press section 26A. Generally the examinee W feels pain more readily when the breast N of the examinee W is harder and thus the value of the breast elasticity is higher. Thus in such cases a value is accordingly derived as a larger deformation amount of the press section 26A at the front-face side (chest wall side). However, generally the examinee W feels pain less readily when the breast N of the examinee W is softer and thus the value of the breast elasticity is lower. Thus in such cases a value is accordingly derived as a smaller deformation amount of the press section 26A at the front-face side (chest wall side). For a similar reason to those when deriving the breast elasticity, a table is also employed for the derivation of the deformation amount of the press section 26A, to derive the deformation amount of the press section 26A from values of the breast elasticity. Such a table is pre-stored in the storage section 47 of the radiographic imaging apparatus 10, illustrated in FIG. 4. Similarly to the derivation of the breast elasticity, configuration may also be made such that derivation of the deformation amount of the press section 26A is derived by computation or by using a dedicated circuit.

Next, based on the derived deformation amount of the press section 26A, an adjustment is performed of the support force to the press section 26A by the reaction force section 26C of the press plate 26 (S18). In such an adjustment of the support force, data of the deformation amount of the press section 26A is read into the imaging apparatus controller 48 from a table stored in the storage section 47 of the radiographic imaging apparatus 10 as described above and illustrated in FIG. 4. In the imaging apparatus controller 48, control of drive force of the drive source 264 is performed according to data of this change amount. The drive force of the drive source 264 is transmitted to the reaction force adjustment mechanism 268 illustrated in FIG. 5, FIG. 6 and FIG. 8. In the reaction force adjustment mechanism 268, the drive force of the drive source 264 is transmitted respectively to the gear wheel 268A, the gear wheel 268B, the rotation transmission shaft 268C and the reels 268D. An extension or contraction of the resilient bodies 268E arises when rolling up or letting out of the coupling lines 268F is performed by the reels 268D, thereby adjusting the support force F2 to the press section 26A from the reaction force section 26C. The adjustment of the support force F2 is, for example, performed by adjusting the drive amount of the drive source 264, for example by adjusting the number of rotations in cases in which an electrical motor is employed for the drive source 264.

The manual adjustment section 269 is operated by an operator in cases in which the adjustment of the deformation amount of the press section 26A is not made automatically, or for cases in which a fine adjustment is made manually. The coupling between the drive source 264 and the gear wheel 268A of the transmission section is released by the clutch 266 during the operation of the manual adjustment section 269.

At step S10, when there is consultation history of the examinee W, since there is data for determining the deformation amount of the press section 26A of the press plate 26 already stored in the storage section 47, illustrated in FIG. 4, this data is input from the storage section 47 to the imaging apparatus controller 48 (S24). At step S18, an adjustment of the support force of the press section 26A from the reaction force section 26C is performed in a similar manner based on this data. Note that the data for determining the deformation amount may be input through the operation panel 46 by a doctor or operator.

Next, an adjustment of the support force F2 of the reaction force section 26C is performed and the positioning pressing of the breast N of the examinee W using the press plate 26 with the adjusted press section 26A deformation amount is performed (S20). The positioning pressing is the pressing executed during actual radiographic image capture, and the breast N is pressed with a pressing force of for example about 80N to 120N. A portion of the press section 26A is formed with the local surface profile so as to project out towards the imaging face 20 side, thereby enabling the breast N to be pressed evenly overall by the positioning pressing. Note that the deformation amount of the press section 26A of the press plate 26 has been adjusted to optimize according to the hardness of the breast N. The examinee W is accordingly unlikely to feel pain even though the breast N is being pressed.

In the state of positioning pressing, bremsstrahlung radiation is then irradiated from the radiation irradiation section 24 illustrated in FIG. 1 towards the breast N, and a radiographic image of the breast N is captured through the radiation detector 42 of the imaging table 22 (S22). Then, the breast N pressed by the press plate 26 is released, thereby completing the image capture.

Operation and Advantageous Effects of the First Exemplary Embodiment

In the press plate 26 according to the first exemplary embodiment, the reaction force section 26C is provided so as to enable support of the resilient deformable press section 26A, and hence the support force from the reaction force section 26C to the press section 26A is variable. According to the change of the support force to the press section 26A, a change also occurs in the reaction force of the press section 26A. The deformation amount of the press section 26A can accordingly be adjusted by changing the reaction force of the press section 26A. Consequently, the deformation amount of the press section 26A can be optimized for the pressed state with the same pressing force due to the press plate 26. For example, in the press plate 26 attached to the radiographic imaging apparatus 10 serving as mammography equipment, the deformation amount of the press section 26A can be adjusted according to the characteristics of the breast N, even in cases in which the breast N of the examinee W is interposed between the imaging face 20 of the imaging table 22 and the press section 26A and is pressed with the same pressing force. Thus by making the deformation amount of the press section 26A larger for an examinee W who is more susceptible to feeling pain, the pain felt by the examinee W can be reduced.

Moreover, the reaction force adjustment mechanism 268 is provided in the press plate 26 according to the first exemplary embodiment, and hence the support force of the reaction force section 26C can be varied.

Moreover, in the press plate 26 according to the first exemplary embodiment, the press section 26A and the support section 26B are formed from the same member, and so the press section 26A can be formed by making the thickness thinner than the thickness of the support section 26B. It is accordingly possible to manufacture the press plate 26 using a simple structure.

Moreover, in the press plate 26 according to the first exemplary embodiment, one end portion of the reaction force section 26C is capable of supporting the press section 26A, and another end portion is coupled to the reaction force adjustment mechanism 268, and the intermediate portion is rotatably provided to the support section 26B, thereby enabling a simple structure. This accordingly enables the press plate 26 to be manufactured using a simple structure.

Moreover, in the press plate 26 of the first exemplary embodiment, when the breast N (image capture body), that is softer than the press section 26A and that has a local surface profile that projects out towards the press section 26A side, is interposed between the imaging face 20 and the press section 26A, a central portion of the breast N is pressed by the local surface profile of the press section 26A and the vicinity of the central portion is spread out. The thickness of the breast N interposed between the imaging face 20 and the press section 26A can thereby be made uniform.

Moreover, in the press plate 26 according to the first exemplary embodiment, the reaction force adjustment mechanism 268 is configured with the resilient bodies 268E, and the adjustment section that adjusts extension or contraction of the resilient bodies 268E. The structure of the reaction force adjustment mechanism 268 is accordingly simplified, enabling the press plate 26 to be manufactured with a simpler structure.

Moreover, in the press plate 26 according to the first exemplary embodiment, the adjustment section is equipped with the coupling lines 268F, the reels 268D, the drive source 264 and the transmission section, and thus the support force of the reaction force section 26C can be adjusted by the use of the drive force from the drive source 264. Consequently, the adjustment of the support force of the reaction force section 26C, and hence the adjustment of the deformation amount of the press section 26A, can be automated.

In the press plate 26 according to the first exemplary embodiment, the manual adjustment section 269 coupled to the adjustment section is provided, and so using the manual adjustment section 269, a manual adjustment can be made to the support force of the reaction force section 26C and to the deformation amount of the press section 26A, separately from the drive force from the drive source 264.

Moreover, in the radiographic imaging apparatus 10 according to the first exemplary embodiment, the press plate 26, the imaging table 22, the radiation irradiation section 24 and the imaging apparatus controller 48 are provided, and the imaging apparatus controller 48 is configured to control the drive force of the drive source 264 to adjust the support force of the reaction force section 26C through the reaction force adjustment mechanism 268. Consequently, the support force of the reaction force section 26C and the deformation amount of the press section 26A can be automatically adjusted using the imaging apparatus controller 48.

Moreover, in the radiographic imaging apparatus 10 according to the first exemplary embodiment, the support force of the reaction force section 26C and the deformation amount of the press section 26A are adjusted by the imaging apparatus controller 48 based on breast thickness, or pressing force, or both. Hence the deformation amount of the press section 26A can be automatically adjusted according to the examinee W.

Second Exemplary Embodiment

Explanation follows regarding an example in which the adjustment of the deformation amount of the press section 26A of the press plate 26 in a radiographic imaging apparatus 10 according to the first exemplary embodiment is implemented in a second exemplary embodiment of the present invention based on human tissue of an image capture body.

Operation of Radiographic Imaging Apparatus and Press Plate

Figure 11:
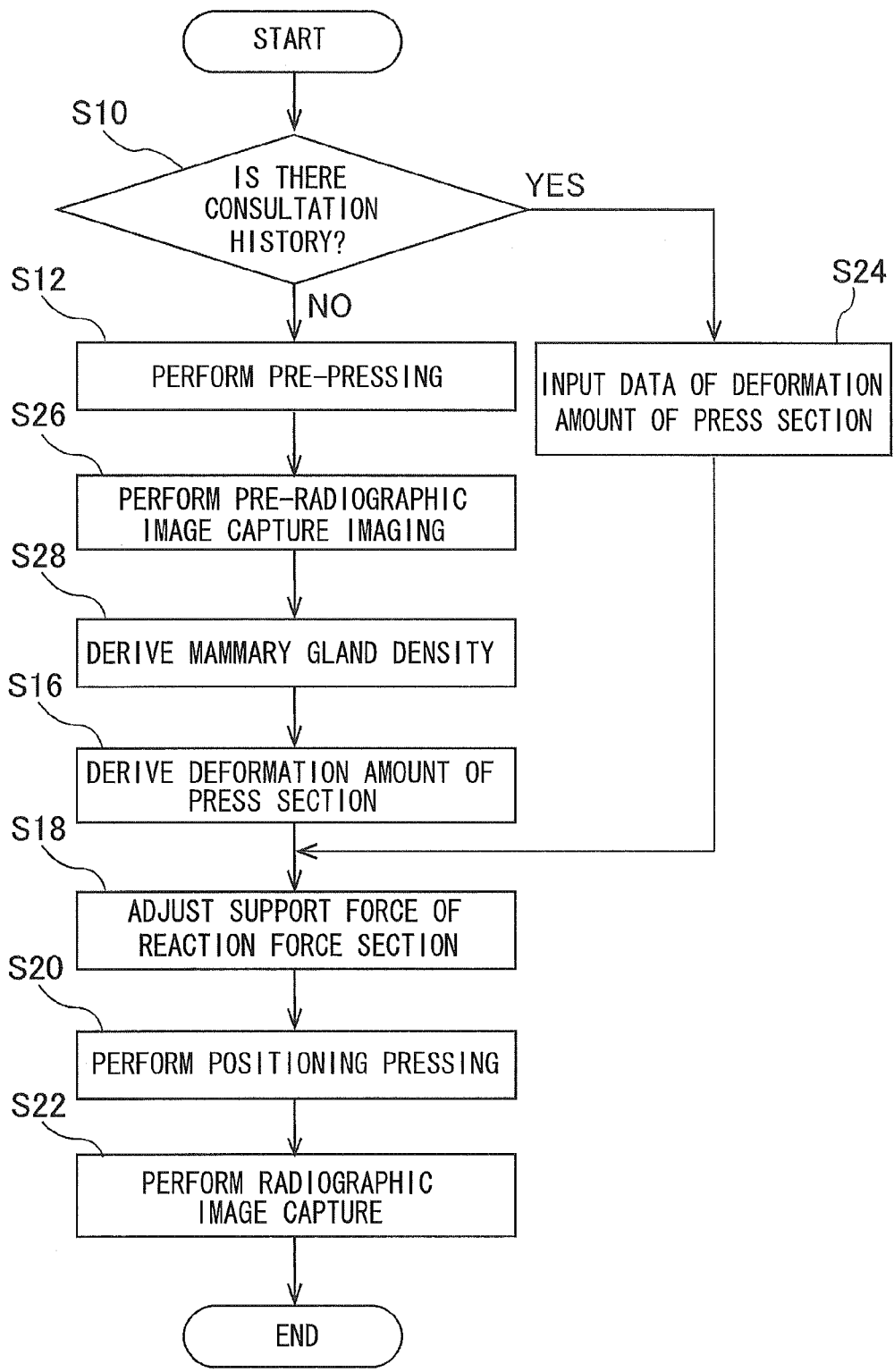
FIG. 11 is a control flow chart of a radiographic imaging apparatus according to a second exemplary embodiment of the present invention.

Operation of a radiographic imaging apparatus 10 and a press plate 26 according to the second exemplary embodiment is as follows. As illustrated in FIG. 11, similarly to the operation of the radiographic imaging apparatus 10 and the press plate 26 in the first exemplary embodiment, the pre-pressing of step S12 is executed in cases in which there is no consultation history as a result of determination of consultation history at step S10.

After the pre-pressing, pre-radiographic image capture is executed (S26). The pre-radiographic image capture is the radiographic imaging performed with the amount of radiation that enables at least the density of human tissue of the breast N of the examinee W, in this case the mammary gland density, to be measured. Thus the amount of radiation for the pre-radiographic image capture is set lower than the radiation amount for the actual radiographic image capture at step S22. For example, the radiation amount may be set at 0.2 mGy for the pre-radiographic image capture and it is set at 2 mGy for the radiographic image capture.

The mammary gland density of the breast N is derived based on a radiographic image obtained by the pre-radiographic image capture (S28). The image of the breast N captured by irradiation of X-rays from the side of the examinee W is schematically illustrated in 6 samples from FIG. 12A to FIG. 12F. The locations of mammary glands are illustrated inside the breast N. The proportion of mammary gland per unit volume (per unit of cross-sectional area in the illustration) increases on progression from sample in FIG. 12A to sample in FIG. 12F. In the images of X-ray image capture, the mammary gland density can be computed from a ratio of the area of the mammary gland to the breast N cross-sectional area. For example, there is a tendency for the mammary gland density (%) to increase on progression from the sample illustrated in FIG. 12A towards the sample illustrated in FIG. 12F. With reference to the mammary gland density of the breast N in the sample illustrated in FIG. 12A, the mammary gland density of the sample illustrated in FIG. 12B is 5% to 10% higher than that of the sample in FIG. 12A, the mammary gland density of the sample illustrated in FIG. 12C is 15% to 20% higher than that of the sample in FIG. 12A, the mammary gland density of the sample illustrated in FIG. 12D is 25% to 40% higher than that of the sample in FIG. 12A, mammary gland density of the sample illustrated in FIG. 12F is 50% to 70% higher than that of the sample in FIG. 12A, and the mammary gland density of the sample illustrated in sample in FIG. 12F is 75% to 80% higher than that of the sample in FIG. 12A.

When the mammary gland density of the breast N has been derived, the deformation amount of the press section 26A of the press plate 26 is then derived, as illustrated in FIG. 12G (S16). In FIG. 12G, the horizontal axis is the mammary gland density (%) and, similarly to the vertical axis of FIG. 10B, the vertical axis is the deformation amount of the press section 26A (mm). In cases in which with mammary gland density of the breast N of the examinee W is high, the breast N is harder, and generally pain is comparatively easily caused to the examinee W. Thus in such cases a value is derived such that the deformation amount of the front-face side of the press section 26A is larger. On the other hand, in cases in which the mammary gland density of the breast N of the examinee W is lower, the breast N is softer, and generally pain is comparatively less readily caused to the examinee W. Thus in such cases a value is derived such that the deformation amount of the front-face side of the press section 26A is smaller. Thus for the similar reasons to those when deriving the breast elasticity of the first exemplary embodiment, a table is employed to derive the deformation amount, to derive a deformation amount from the value of the mammary gland density. Such a table is pre-stored in a storage section 47 of the radiographic imaging apparatus 10, as already illustrated in FIG. 4. Configuration may also be made such that the derivation of the deformation amount is the derivation by computing or the derivation using a dedicated circuit.

Next, an adjustment to the support force of the reaction force section 26C is performed based on the derived deformation amount (S18). This adjustment method is similar to the adjustment method for support force of the reaction force section 26C in the first exemplary embodiment. Note that in cases in which there is consultation history of the examinee W at step S10, appropriate data is input at step S24. Then at step S18, an adjustment is performed as to the support force of the reaction force section 26C based on the input data.

Next, the positioning pressing of the breast N of the examinee W is executed by the press plate 26 of which the support force of the reaction force section 26C and the deformation amount of the press section 26A have been adjusted (S20). In the positioning pressing, the deformation amount of the press section 26A of the press plate 26 is optimally adjusted according to the mammary gland density of the breast N. Thus pain is not likely to be caused to the examinee W even though the breast N is pressed.

In the state of positioning pressing, bremsstrahlung radiation is irradiated from the radiation irradiation section 24 illustrated in FIG. 1 towards the breast N, and a radiographic image of the breast N is captured using the radiation detector 42 of the imaging table 22 (S22). Then, the breast N pressed by the press plate 26 is released, thereby completing the image capture.

Operation and Advantageous Effects of Second Exemplary Embodiment

In the press plate 26 and the radiographic imaging apparatus 10 according to the second exemplary embodiment, operation and advantageous effects can be obtained, which are similar to those obtained from the press plate 26 and the radiographic imaging apparatus 10 of the first exemplary embodiment.

Moreover, in the radiographic imaging apparatus 10 according to the second exemplary embodiment, the adjustment of the support force of the reaction force section 26C is controlled by the imaging apparatus controller 48 based on the density of human tissue, or more specifically, on the density of the mammary gland density data. Thus the deformation amount of the press section 26A of the press plate 26 can be automatically adjusted according to the breast N of the examinee W.

Note that although in the second exemplary embodiment the mammary gland density is employed as the density of human tissue, there is no limitation thereto. For example, tissue such as subcutaneous fat or Cooper's ligament may be employed as human tissue. Moreover, with respect to derivation of the density of human tissue, there is also no limitation to using radiographic image capture, and the combined use of ultrasound detection is possible.

Third Exemplary Embodiment

Explanation follows regarding a third exemplary embodiment of the present invention, this being an example in which the adjustment of deformation amount of the press section 26A of the press plate 26 in the radiographic imaging apparatus 10 according to the second exemplary embodiment is executed based on a radiation transmissivity of an image capture body.

Overall Configuration of Radiographic Imaging Apparatus

Figure 13:
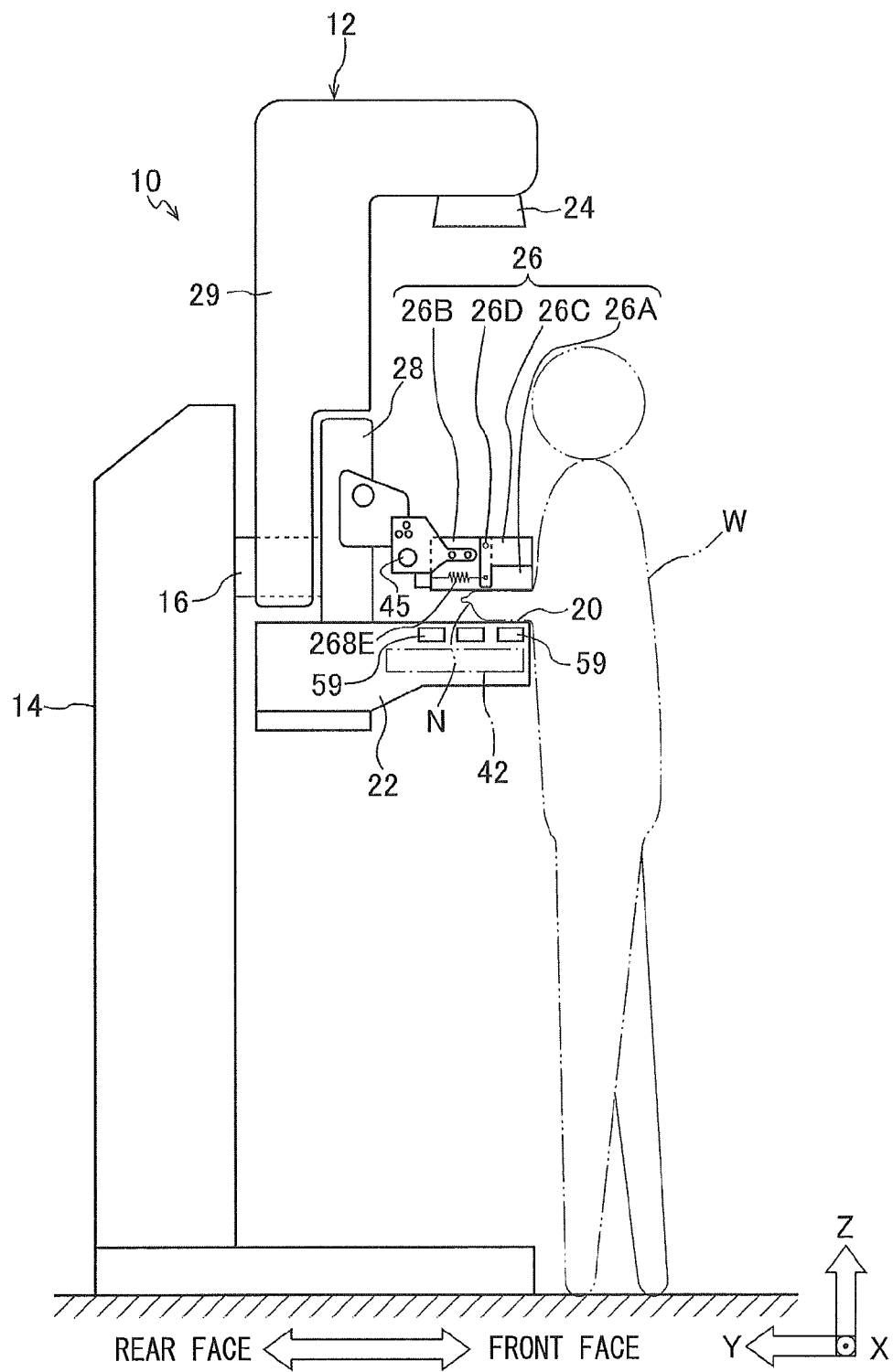
FIG. 13 is a schematic side view for explaining an overall configuration of a radiographic imaging apparatus according to a third exemplary embodiment of the present invention.
Figure 14:
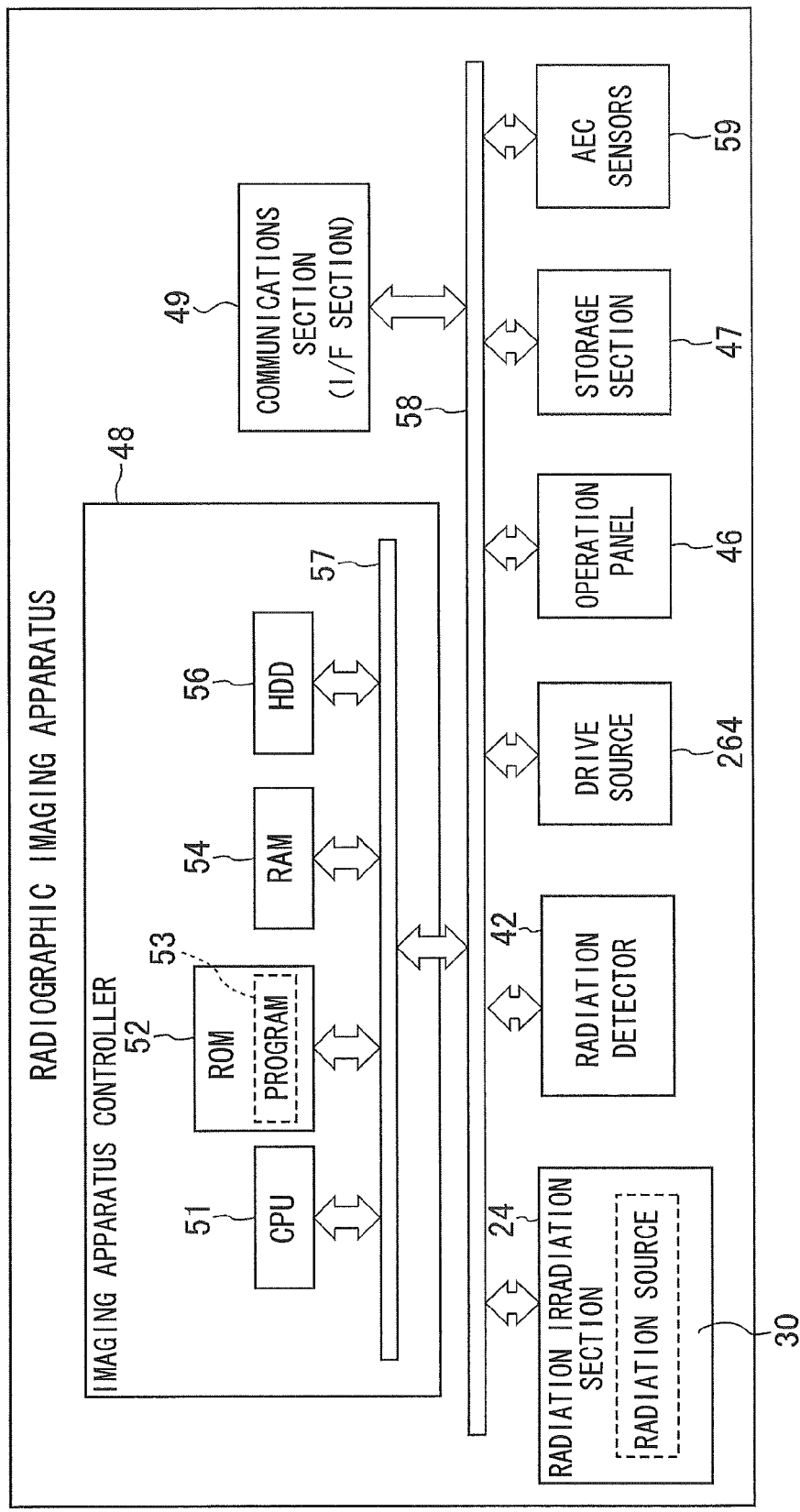
FIG. 14 is an overall system block diagram of the radiographic imaging apparatus illustrated in FIG. 13.

As illustrated in FIG. 13, a radiographic imaging apparatus 10 according to a third exemplary embodiment is provided with Automatic Exposure Controller (AEC) sensors 59, which are built inside an imaging table 22 and between an imaging face 20 and a radiation detector 42. Plurality of the individual AEC sensors 59 are disposed in a matrix shape in plan view of the imaging face 20, although not illustrated in the drawings. For example, there are 9 individual AEC sensors 59 disposed 3 by 3 across in the X direction and across in the Y direction. As illustrated in FIG. 14, the AEC sensors 59 are connected to the imaging apparatus controller 48 and other sections through the common bus 58.

Operation and Advantageous Effects of Radiographic Imaging Apparatus

At step S26 of a control flow chart illustrated in FIG. 11 for the radiographic imaging apparatus 10 according to the second exemplary embodiment, the AEC sensors 59 are irradiated in the pre-radiographic image capture, and the radiation amount that has passed through the breast N of the examinee W is measured. Moreover, the thickness of the breast N is measured at the time the radiation amount is measured. The radiation transmissivity of the breast N can be derived based on the result of measuring the radiation amount and the thickness of the breast N. This radiation transmissivity can be easily derived in the imaging apparatus controller 48 from the measurement result of the radiation amount transmitted from the AEC sensors 59, and from the thickness of the breast N input through the operation panel 46. Similarly to in the radiographic imaging apparatus 10 according to the first exemplary embodiment, any method out of a table, computation or a dedicated circuit are employable as the derivation method.

After the radiation transmissivity of the breast N has been derived, the deformation amount of the press plate 26 is derived based on this transmissivity. For example, in cases in which the radiation transmissivity of the breast N of the examinee W is low due to the high mammary gland density, the breast N is harder, and generally pain is comparatively more easily caused to the examinee W. Thus a value is derived such that there is a large deformation amount at the front-face side of the press section 26A. However, in cases in which there is a low mammary gland density of the breast N of the examinee W and the radiation transmissivity is high, the breast N is softer, and generally pain is less liable to be caused to the examinee W. Thus a value is derived such that there is a small deformation amount at the front-face side of the press section 26A. For similar reasons to those in derivation of breast elasticity in the first exemplary embodiment, a table may be employed for the deformation amount derivation that derives the deformation amount from the value of the radiation transmissivity and the thickness of the breast N. Such a table is pre-stored in a storage section 47 of the radiographic imaging apparatus 10, as illustrated in FIG. 4. Moreover, the derivation of the deformation amount of the press section 26A may be the derivation by computation or the derivation by dedicated circuit.

Processing from step S18 afterwards of the control flow chart illustrated in FIG. 11 is then executed, and a radiographic image of the breast N is captured.

Operation and Advantageous Effects of the Third Exemplary Embodiment

According to the press plate 26 and the radiographic imaging apparatus 10 according to the third exemplary embodiment, similar operation and advantageous effects may be obtained to those obtained by the press plate 26 and the radiographic imaging apparatus 10 according to the second exemplary embodiment.

Moreover, in the radiographic imaging apparatus 10 according to the third exemplary embodiment, the support force of the press section 26A from the reaction force section 26C is controlled by the imaging apparatus controller 48 based on the radiation transmissivity data. Thus the deformation amount of the press section 26A of the press plate 26 can be adjusted automatically according to the breast N of the examinee W.

Fourth Exemplary Embodiment

Explanation follows regarding a fourth exemplary embodiment of the present invention, this being a modified example of the press plate 26 according to any one of the first to the third exemplary embodiments.

Configuration of Press Plate

Figure 15:
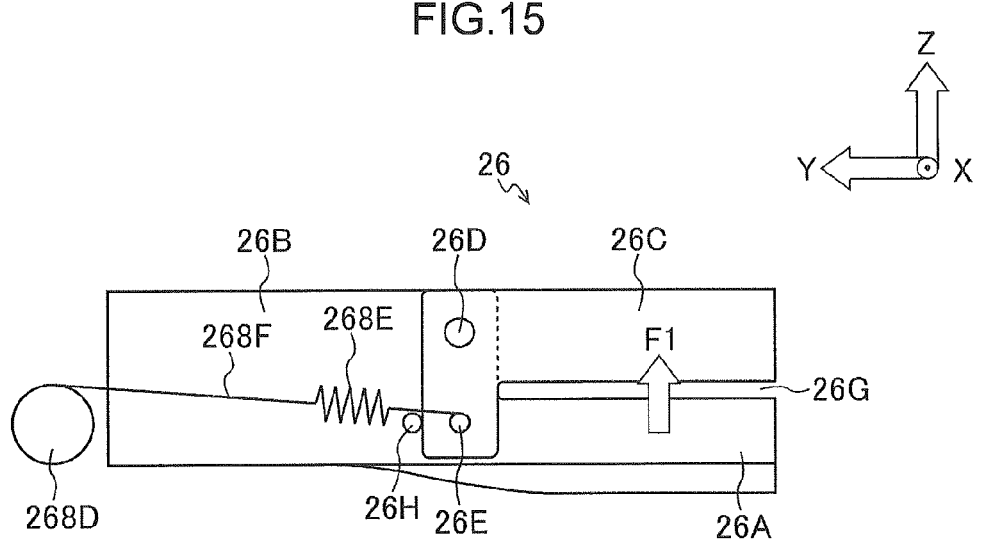
FIG. 15 is a schematic side view, corresponding to FIG. 7A and FIG. 7B, of a press plate of a radiographic imaging apparatus according to a fourth exemplary embodiment of the present invention.

In the press plate 26 according to the fourth exemplary embodiment, there is a stopper section 26H provided as illustrated in FIG. 15, such that one end portion of the reaction force section 26C does not rotate more than a fixed amount towards the press section 26A side, and a gap 26G is provided between the press section 26A and the one end portion of the reaction force section 26C.

Operation and Advantageous Effects of the Fourth Exemplary Embodiment

In the press plate 26 according to the fourth exemplary embodiment, the gap 26G enables resilient deformation of the press section 26A according to the coefficient of elasticity of the press section 26A until the press section 26A starts to be supported by the reaction force section 26C. When the press section 26A is supported by the reaction force section 26C, the deformation amount of press section 26A becomes smaller according to the support force of the reaction force section 26C, however the deformation amount of the press section 26A is larger when not supported by the reaction force section 26C. Thus for an examinee W who feels pain, pain felt by the examinee W can be reduced by making the deformation amount of the press section 26A larger at the initial stage of starting pressing.

Fifth Exemplary Embodiment

Explanation follows regarding a fifth exemplary embodiment of the present invention, this being a further modified example of the press plate 26 according to the fourth exemplary embodiment.

Configuration of Press Plate

Figure 16:
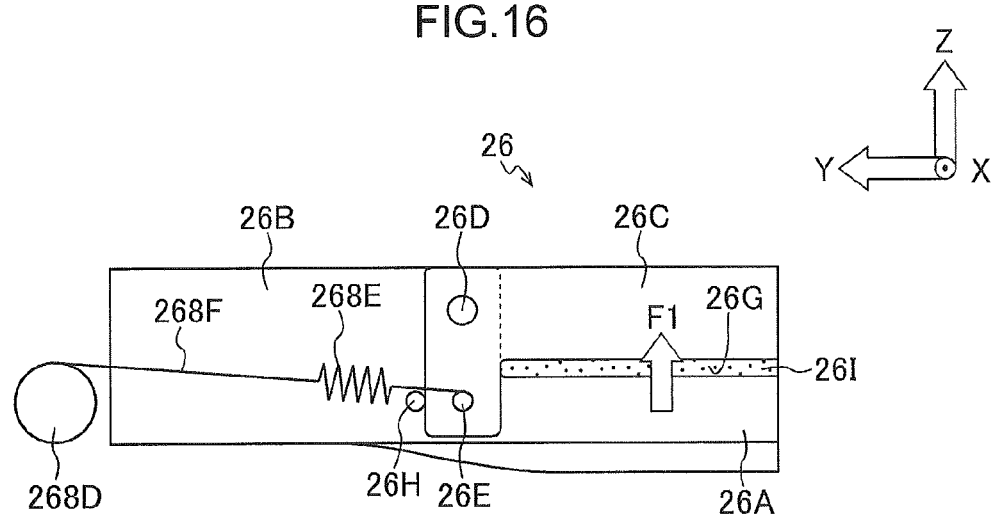
FIG. 16 is a schematic side view, corresponding to FIG. 7A and FIG. 7B, of a press plate of a radiographic imaging apparatus according to a fifth exemplary embodiment of the present invention.

A press plate 26 according to the fifth exemplary embodiment, as illustrated in FIG. 16, has a gap member 261 provided in the gap 26G, the gap member 261 having a smaller coefficient of elasticity than the press section 26A and the support section 26B. The gap member 261 is provided over the whole area of the gap 26G in this case, however the gap member 261 may be provided to only a part of the front-face side (the chest wall side). A soft member such as for example rubber or sponge is employed as the gap member 261. Such a soft member is adhered to one or other of the press section 26A or the reaction force section 26C using for example an adhesive.

Operation and Advantageous Effects of the Fifth Exemplary Embodiment

In the press plate 26 of the first exemplary embodiment, the gap member 261 enables resilient deformation of the press section 26A according to the coefficient of elasticity of the gap member 261 and the press section 26A until the press section 26A starts to be supported by the reaction force section 26C. When the press section 26A is supported by the reaction force section 26C, the deformation amount of press section 26A becomes smaller, however the deformation amount of the press section 26A is larger when not supported by the reaction force section 26C. Thus for an examinee W who feels pain, pain felt by the examinee W can be reduced by making the deformation amount of the press section 26A larger at the initial stage of starting pressing. Moreover, due to the gap 26G in the press plate 26 according to the fifth exemplary embodiment being filled with the gap member 261, trapping of the examinee W in the gap 26G can be prevented.

Other Exemplary Embodiments

Although plural exemplary embodiments of the present ion have been explained above, the present invention is not limited by the above exemplary embodiments, and various modifications are possible within a scope not departing from the spirit of the present invention. For example, in the present invention, a press plate 26 and a radiographic imaging apparatus 10 may be configured with a structure that is a combination of elements from 2 or more of the first exemplary embodiment to the fifth exemplary embodiment.

Moreover, although X-rays are employed as radiation in the above exemplary embodiments, there is no limitation thereto. The present invention includes at least radiations such as gamma rays, an electron beam, a neutron beam, a proton beam and a heavy particle beam that are used in medical consultation. Moreover, an explanation has been given in the above exemplary embodiments of examples in which the radiographic imaging apparatus and the press plate are applied to mammography equipment and press plate for mammography equipment, however there is no limitation thereto. For example, the present invention may be applied to a press plate that presses a stomach region in order to perform X-ray imaging such as of a gastrointestinal image capture body, or to an X-ray radiographic imaging apparatus incorporating such a press plate.

Due to the present invention being configured as described above, a press plate capable of achieving an optimum deformation amount for the pressed state with the same pressing force, and a radiographic imaging apparatus of the same can be provided.

What is claimed is:

1. A press plate comprising:
   a press section that is disposed to face towards an imaging face of an imaging table and is resiliently deformable; and
   a reaction force section that has a variable support force of the press section at the opposite side to the imaging face, and that adjusts a magnitude of a deformation amount, due to a resilient deformation, of the press section in a pressed state with the same pressing force.

2. The press plate according to claim 1, further comprising a reaction force adjustment mechanism that changes the support force of the reaction force section.

3. The press plate according to claim 2, further comprising a support section that is integrally provided to a first end of the press section, wherein the first end portion of the reaction force section is capable of supporting the press plate, a second end portion of the reaction force section is coupled to the reaction force adjustment mechanism, and an intermediate portion of the reaction force section is rotatably provided to the support section.

4. The press plate of claim 3, wherein:
   the first end portion of the reaction force section comprises a stopper portion that stops rotation more than a fixed amount towards the press section side; and
   a gap is provided between the press section and the first end portion of the reaction force section.

5. The press plate of claim 4, wherein:
   a gap member that has a smaller coefficient of elasticity than the press section and the support section is provided in the gap.

6. The press plate of claim 2, wherein the press section comprises a local surface profile that projects out towards the imaging face side.

7. The press plate of claim 2, wherein the reaction force adjustment mechanism comprises:
   a resilient body that has a first end connected to the reaction force section and that biases the reaction force section with a support force; and
   an adjustment section that is connected to a second end of the resilient body and that adjusts extension and contraction of the resilient body.

8. The press plate of claim 7, wherein the adjustment section comprises:
   a coupling line that is connected to the second end of the resilient body;
   a reel that rolls up or lets out the coupling line;
   a drive source that generates drive force for rolling up or letting out of the reel; and
   a transmission section that couples together the drive source and the reel so that drive force from the drive source is transmitted to the reel.

9. The press plate of claim 8, further comprising a manual adjustment section that is coupled to the adjustment section.

10. An radiographic imaging apparatus comprising:
    the press plate of claim 8;
    an imaging table that has an imaging face that faces towards the press section of the press plate;
    a radiation irradiation section that is disposed facing through the press plate towards the imaging table; and
    an imaging apparatus controller that adjusts the support force of the reaction force section through the reaction force adjustment mechanism by controlling the drive force of the drive source.

11. The radiographic imaging apparatus of claim 10, wherein:
    the imaging apparatus controller adjusts the support force using the reaction force adjustment mechanism based on at least one type of data among pressed thickness of an image capture body when the image capture body is disposed on the imaging face and is being pressed by the press plate, pressing force of the press plate, radiation transmissivity of the image capture body, and density of human tissue of the image capture body.

12. The radiographic imaging apparatus of claim 11, wherein:
    the press plate further includes a movable support point portion that is movable between the press section and the support section so that a deformation amount of the press section is adjusted by such movement,
    the density of human tissue comprises density of mammary gland density data, and when the density of the mammary gland density data is higher, the movable support portion is moved and positioned so that the deformation amount is larger.

13. The press plate according to claim 1, wherein one end portion of the reaction force section, which is a front end side portion, is supportable for the press section at an opposite side of the press section to the imaging face.

14. The press plate according to claim 1, wherein the reaction force section is formed in a substantially L-shape in a side view.

15. The press plate according to claim 1, further comprising a support section that is integrally provided to a first end of the press section,
  wherein an intermediate portion of the reaction force section is attached to the support section through a rotation shaft such that the reaction force section is rotatable about the rotation shaft.

16. The press plate according to claim 1, wherein a coefficient of elasticity of a material of the reaction force section is greater than a coefficient of elasticity of a material of the press section.

* * * * *